US010941410B2

(12) United States Patent
Page et al.

(10) Patent No.: US 10,941,410 B2
(45) Date of Patent: Mar. 9, 2021

(54) NUCLEIC ACID SEQUENCES ENCODING TRANSCRIPTION FACTORS REGULATING ALKALOID BIOSYNTHESIS AND THEIR USE IN MODIFYING PLANT METABOLISM

(71) Applicant: 22ND CENTURY LIMITED, LLC, Williamsville, NY (US)

(72) Inventors: Jonathan Page, Saskatoon (CA); Andrea T. Todd, Saskatoon (CA)

(73) Assignee: 22nd Century Limited, LLC, Williamsville, NY (US)

( * ) Notice: Subject to any disclaimer, the term of this patent is extended or adjusted under 35 U.S.C. 154(b) by 136 days.

(21) Appl. No.: 15/996,064

(22) Filed: Jun. 1, 2018

(65) Prior Publication Data

US 2018/0355365 A1 Dec. 13, 2018

Related U.S. Application Data

(62) Division of application No. 14/681,073, filed on Apr. 7, 2015, now Pat. No. 9,988,640, which is a division of application No. 14/261,240, filed on Apr. 24, 2014, now Pat. No. 9,121,030, which is a division of application No. 12/601,752, filed as application No. PCT/IB2008/003131 on May 23, 2008, now Pat. No. 8,822,757.

(60) Provisional application No. 60/924,675, filed on May 25, 2007.

(51) Int. Cl.
*C12N 15/82* (2006.01)
*C07K 14/415* (2006.01)
*A24B 15/10* (2006.01)
*A24B 15/12* (2006.01)

(52) U.S. Cl.
CPC .......... *C12N 15/8243* (2013.01); *A24B 15/10* (2013.01); *A24B 15/12* (2013.01); *C07K 14/415* (2013.01)

(58) Field of Classification Search
CPC .......................... C12N 15/8243; C07K 14/415
See application file for complete search history.

(56) References Cited

U.S. PATENT DOCUMENTS

| 4,407,956 | A | 10/1983 | Howell |
|---|---|---|---|
| 5,294,593 | A | 3/1994 | Khan |
| 5,326,563 | A | 7/1994 | Spindler et al. |
| 5,459,252 | A | 10/1995 | Conkling et al. |
| 5,837,848 | A | 11/1998 | Ely et al. |
| 5,837,876 | A | 11/1998 | Conkling et al. |
| 6,586,661 | B1 | 7/2003 | Conkling et al. |
| 6,602,986 | B1 | 8/2003 | Stemmer et al. |
| 6,703,539 | B1 | 3/2004 | Wilfred et al. |
| 7,217,865 | B2 | 5/2007 | Weaver et al. |
| 7,229,829 | B2 | 6/2007 | Dinesh Kumar et al. |
| 7,700,834 | B2 | 4/2010 | Xu et al. |
| 8,759,101 | B2 | 6/2014 | Timko et al. |
| 8,791,329 | B2 | 7/2014 | Hashimoto et al. |
| 8,822,757 | B2 | 9/2014 | Page et al. |
| 9,121,030 | B2 | 9/2015 | Page et al. |
| 9,157,089 | B2 | 10/2015 | Page et al. |
| 9,157,090 | B2 | 10/2015 | Page et al. |
| 9,719,103 | B2 | 8/2017 | Hashimoto et al. |
| 2002/0197688 | A1 | 12/2002 | Pandolfino |
| 2003/0084473 | A1 | 5/2003 | Gocal et al. |
| 2003/0106105 | A1 | 6/2003 | Hoffmann et al. |
| 2004/0107455 | A1 | 6/2004 | Rommens et al. |
| 2005/0010974 | A1 | 1/2005 | Milligan et al. |
| 2005/0072047 | A1 | 4/2005 | Conkling et al. |
| 2005/0097633 | A1 | 5/2005 | Diehn et al. |
| 2006/0041962 | A1 | 2/2006 | Inze et al. |
| 2007/0034220 | A1* | 2/2007 | Pandolfino ......... C12N 15/8243 131/364 |
| 2007/0266459 | A1* | 11/2007 | Chattopadhyay .. C12N 15/8261 800/289 |
| 2007/0298481 | A1 | 12/2007 | Sato |
| 2015/0218575 | A1 | 8/2015 | Hashimoto et al. |
| 2019/0017062 | A1 | 1/2019 | Page et al. |

FOREIGN PATENT DOCUMENTS

| CN | 1292822 A | 4/2001 |
|---|---|---|
| CN | 1514685 A | 7/2004 |
| CN | 1719971 A | 1/2006 |
| CN | 1719971 A | 1/2006 |
| CN | 1882686 A | 12/2006 |
| WO | WO 2000/52168 | 9/2000 |
| WO | WO 2001/59086 A2 | 8/2001 |
| WO | WO 2002/38588 A2 | 5/2002 |
| WO | WO 2003/013226 A2 | 2/2003 |
| WO | WO 03/020936 A1 | 3/2003 |
| WO | WO 2003/097790 A2 | 11/2003 |
| WO | WO 2004/076625 A2 | 9/2004 |
| WO | WO 2005/001050 | 1/2005 |
| WO | WO 2006/109197 A2 | 10/2006 |
| WO | WO 2008/008844 A2 | 1/2008 |
| WO | WO 2008/020333 A2 | 2/2008 |

OTHER PUBLICATIONS

Facchini, Peter J., David A. Bird, and Benoit St-Pierre. "Can *Arabidopsis* make complex alkaloids?." Trends in plant science 9.3 (2004): 116-122. (Year: 2004).*
Yadav, Vandana, et al. "A basic helix-loop-helix transcription factor in *Arabidopsis*, MYC2, acts as a repressor of blue light-mediated photomorphogenic growth." The Plant Cell 17.7 (2005): 1953-1966. (Year: 2005).*
Office Action issued in co-pending U.S. Appl. No. 15/985,146, dated Jun. 27, 2019.
Shukla et al., "Expression of CAP2, an APETALA2-family transcription factor from chickpea, enhances growth and tolerance to dehydration and salt stress in transgenic tobacco," *Plant Physiology*, vol. 142, pp. 113-123 (2006).

(Continued)

*Primary Examiner* — Weihua Fan
(74) *Attorney, Agent, or Firm* — Foley & Lardner LLP

(57) ABSTRACT

Plant metabolism and alkaloid levels can be regulated by transcription factors that regulate the nicotinic alkaloid biosynthetic pathway. In one embodiment, the disclosure provides a transcription factor that negatively regulates alkaloid biosynthesis, such as nicotine biosynthesis.

13 Claims, 4 Drawing Sheets

Specification includes a Sequence Listing.

(56) References Cited

OTHER PUBLICATIONS

Office Action issued in co-pending Chinese Patent Application No. 201610092006.5, dated Dec. 27, 2018.
Official Action issued in co-pending Chinese Patent Application No. 201610091915.7, dated Feb. 27, 2019.
Notice of Allowance issued in co-pending U.S. Appl. No. 15/658,236, dated Feb. 20, 2019.
Corrected Notice of Allowability issued in co-pending U.S. Appl. No. 15/658,236, dated May 13, 2019.
Office Action issued in co-pending Canadian Patent Application No. 3,008,999, dated May 6, 2019.
Office Action issued in co-pending U.S. Appl. No. 15/985,146, dated Nov. 19, 2019.
Akira Katoh et al., "Molecular Cloning of N-Methylputrescine Oxidase from Tobacco", Plant Cell Physiol, 48, 3, pp. 550-554, 2007.
Andrew J. Hamilton et al., "A Species of Small Antisense RNA in Posttranscriptional Gene Silencing in Plants", Science , Oct. 29, 1999, vol. 286, pp. 950-952.
Ann Depicker et al., "Post-transcriptional gene silencing in plants", Current Opinion in Cell Biology, 1997, 9, pp. 373-382.
Carol A. Rhodes et al., "Genetically Transformed Maize Plants from Protoplasts", Science, vol. 240, pp. 204-207.
Charles J. Thompson et al., "Characterization of the herbicide-resistance gene bar from Streptomyces hygroscopicus", The EMBO Journal, vol. 6, No. 9, pp. 2519-2523, 1987.
Chris A. Helliwell et al., "Constructs and Methods for Hairpin RNA-Mediated Gene Silencing in Plants", Methods in Enzymology, vol. 392, pp. 24-35.
D. Becker et al., "Fertile transgenic wheat from microprojectile bombardment of scutellar tissue", The Plant Journal, 1994, 5, 2, pp. 299-307.
D.D. Songstad et al., "Advances in alternative DNA delivery techniques", Plant Cell, Tissue and Organ Culture, 40, pp. 1-15, 1995.
David C Baulcombe, "Fast forward genetics based on virus-induced gene silencing", Current Opinion in Plant Biology, 1999, 2: pp. 109-113.
Debora Vom Endt et al., "Transcription factors controlling plant secondary metabolism: what regulates the regulators", Phytochemistry, 61, 2002, pp. 107-114.
Enwu Liu et al., "Optimized cDNA libraries for virus-induced gene silencing (VIGS) using tobacco rattle virus", Plant Methods, 2008, 4, 5, pp. 1-13.
Eugene W. Myers et al., "Optimal alignments in linear space", Cabios, vol. 4, No. 1, 1988, pp. 11-17.
Francis C. Hsu et al., "Phloem Mobility of Xenobiotics VI. A Phloem-Mobile Pro-nematicide Based on Oxamyl Exhibiting Root-Specific Activation in Transgenic Tobacco", Pestic. Sci, 1995, 44, pp. 9-19.
Frank Ratcliff et al., "Tobacco rattle virus as a vector for analysis of gene function by silencing", The Plant Journal, 2001, 25, 2, pp. 237-245.
Fumihiko Sato et al., "Metabolic engineering of plant alkaloid biosynthesis", PNAS, Jan. 2, 2001, vol. 98, No. 1, pp. 367-372.
I. Potrykus, "Gene Transfer to Plants: Assesment of Published Approaches and Results", Annu. Rev. Plant Physiol. Plant Mol. Biol. 1991, 42, pp. 205-225.
Indra K. Vasil, "Molecular improvement of cereals", Plant Molecular Biology, 25, pp. 925-937, 1994.
Inhwan Hwang et al., "An *Arabidopsis thaliana* root-specific kinase homolog is induced by dehydration, ABA, and NaCi", The Plant Journal, 1995, 8, 1, pp. 37-43.
John Draper B.Sc., Ph.D et al., "Plant Genetic Transformation and Gene Expression a Laboratory Manual", Blackwell Scientific Pulications, pp. 1-3, 1988.

John Paul Alvarez et al., "Endogenous and Synthetic MicroRNAs Stimulate Simultaneous, Efficient, and Localized Regulation of Multiple Targets in Diverse Species", The Plant Cell, vol. 18, pp. 1134-1151, May 2006.
Leslie van der Fits et al., "ORCA3, a jasmonate-Responsive Transcriptional Regulator of plant primary and secondary Metabolism", Science, vol. 289, Jul. 14, 2000, pp. 295-297.
Maike Stam et al., "Distinct features of post-transcriptional gene silencing by antisense transgenes in single copy and inverted T-DNA repeat loci", The Plant Journal, 2000, 21, 1, pp. 27-42.
Marc De Block et al., "transformation of *Brassica napus* and *Brassica oleracea* Using Agrobacterium tumefaciens and the Expression of the bar and neo Genes in the Transgenic Plants", Plant Physiol, 1989, 91, pp. 694-701.
Mark J. Zoller et al., "Obligonucleotide-directed mutagenesis using M13-derived vectors: an efficient and general procedure for the production of point mutations in any fragment of DNA", Nucleic Acid Research, vol. 10, No. 20, 1962, pp. 6487-6500.
Maurice M. Moloney et al., "High efficiency transformation of *Brassica napus* using Agrobacterium vectors", Plant Cell Reports, 1989, 8, pp. 238-242.
Narender S. Nehra et al., "Self-fertile transgenic wheat plants regenerated from isolated scutellar tissues following microprojectile bombardment with two distinct gene contructs", The Plant Journal, 1994, 5, 2, pp. 285-297.
Nicole Bechtold et al., "In planta Agrobacterium mediated gene transfer by infiltration of adult *Arabidopsis thaliana* plants", C. R. Acad. Sci. Paris, Sciences de la vie/Life sciences, 1993, 316, pp. 1194-1200.
Peter R. Beetham et al., "A tool for functional plant genemics: Chimeric RNA/DNA oligonucleotides cause in vivo gene-specific mutations", PNAS USA, vol. 96, pp. 8774-8778, Jul. 1999, Plant Biology.
Philip Stegmaier et al., "Systematic DNA-Binding Domain Classification of Transcription Factors", Genome Informatics, 15, 2: pp. 276-286, 2004.
Pierre Broun, "Transcription factors as tools for metabolic engineering in plants", Current Opinion in Plant Biology 2004, 7, pp. 202-209.
Rebecca Schwab et al., "Highly Specific Gene Silencing by Artificial MicroRNAs in *Arabidopsis*", The Plant Cell, vol. 18, pp. 1121-1133, May 2006.
Richard Walden et al., "Transgenesis: altering gene expression and plant development", "Gene-transfer and plant-regeneration techniques", TibTech, Sep. 1995, vol. 13, pp. 324-331.
Robert A. Winz et al., "Molecular Interactions between the Specialist Herbivore Manduca sexta (Lepidoptera, Sphingidae) and Its Natural Host Nicotiana attenuata. IV. Insect-Induced Ethylene Reduces Jasmonate-Induced Nicotine Accumulation by Regulating Putrescine N-Methyltransferase Transcripts 1,2", Plant Physiology, Apr. 2001, vol. 125, pp. 2189-2202.
Rong Li et al., "functional Genomic Analysis of Alkaloid Biosynthesis in Hyoscyamus niger Reveals a Cytochrome P450 Involved in Littorine Rearrangement", Chemistry & Biology, 13, pp. 513-520, May 2006.
Rui Lu, et al., "Virus-induced gene silencing in plants", Methods, 30, 2003, pp. 296-303.
Stephanie Guillon et al., "Hairy root research: recent scenario and exciting prospects", Current opinion in Plant Biology, 2006, 9, pp. 341-346.
Stephen F. Altschul et al., "Gapped BLAST and PSI-BLAST: a new generation of protein database search programs", Nucleic Acids Research, 1997, vol. 25, No. 17, pp. 3389-3402.
Stephen S. Hecht et al., "Tobacco-Specific Nitrosamines: Occurrence, Formation, Carcinogenicity, and Metabolism", American Chemical Society, vol. 12, 1979, pp. 92-98.
Steven Henikoff et al., "TILLING. Traditional Mutagenesis Meets Functional Genomics", Plant Physiology, Jun. 2004, vol. 135, pp. 630-636.
Tong Zhu et al., "Targeted manipulation of maize genes in vivo using chimeric RNA/DNA oligonucleotides", PNAS USA, vol. 96, pp. 8768-8773, Jul. 1999.

(56) References Cited

OTHER PUBLICATIONS

Tsubasa Shoji et al., "Expression patterns of two tobacco isoflavone reductase-like genes and their possible roles in secondary metabolism in tobacco", Plant Molecular Biology, 50, pp. 427-440, 2002.
Tsubasa Shoji et al., "Jasmonate Induction of Putrescine N-Methyltransferase Genes in the Root of Nicotiana sylvestris", Plant Cell Physiol, 41, 7, pp. 831-839, 2000.
Valerie De Sutter et al., "exploration of jasmonate signalling via automated and standardized transient expression assays in tobacco cells", The Plant Journal, 2005, 44, pp. 1065-1076.
Vesna Katavic et al., "In planta transformation of *Arabidopsis thaliana*", Mol Gen Genet, 1994, 245, pp. 363-370.
Wim Broothaerts et al., "Gene transfer to plants by diverse species of bacteria", Nature, vol. 433, Feb. 10, 2005, pp. 629-633.
Xin Li et al., "A fast neutron deletion mutagenesis-based reverse genetics system for plants", The Plant Journal, 2001, 27, 3, pp. 235-242.
Yan-Hua Xu et al., "Characterization of GaWRKY1, a Cotton Transcription Factor That Regulates the Sesquiterpene Synthase Gene (+)-δ-Cadinene Synthase-A1", Plant Physiology, May 2004, vol. 135, pp. 507-515.
Yule Liu et al.,"Tobacco Rar1, EDS1 and NPR1/NIM1 like genes are required for N-Mediated resistance to tobacco mosaic virus", The Plant Journal, 2002, 30, 4, pp. 415-429.
Yupynn Chintapakorn et al., "Antisense-mediated down-regulation of putrescine N-methyltransferase activity in transgenic *Nicotiana tabacum* L. can lead to elevated levels of anatabine at the expense of nicotine", Plant Molecular Biology, 53, pp. 87-105, 2003.
International Search Report PCT/IB2008/003131 dated Jul. 20, 2009.
J. Memelink et al., "Transcription factors involved in terpenoid indole alkaloid biosynthesis in Catharanthus roseus", Phytochem Rev (2007) 6:353-362.
J. Memelink et al., "Transcriptional regulators to modify secondary metabolism", Metabolic Engineering of Plant Secondary Metabolism, 2000, pp. 111-125.
Kevin M. Davies et al., "Transcriptional regulation of secondary metabolism", Functional Plant Biology, 2003, vol. 30, No. 9, pp. 913-925.
China P.R. Application No. 200880100279.3 Official Action dated Jul. 4, 2012.
Gavilano et al., "Functional analysis of nicotine demethylase genes reveals insights into the evolution of modern tobacco", 282 Journal of Biological Chemistry No. 1, 249-256 (2007).
U.S. Appl. No. 13/464,212 Office Action dated Nov. 27, 2012.
Siegmund et al., "Determination of the Nicotine Content of Various Edible Nightshades (Solanaceae) and Their Products and Estimation of the Associated Dietary Nicotine Intake", 47 J. Agric. Food Chem., 3113-3120 (1999).
U.S. Appl. No. 13/464,212, Office Action dated May 3, 2013.
Facchini, "Alkaloid Biosynthesis in Plants: Biochemistry, Cell Biology, Molecular Regulation, and Metabolic Engineering Applications," 52 Annual Review of Plant Physiology and Plant Molecular Biology, pp. 29-66 (2001).
Friedberg, "Automated Protein Function Prediction—the Genomic Challenge," 7 Briefings in Bioinformatics No. 3, pp. 225-242 (2006).
Guo et al., "Protein Tolerance to Random Amino Acid Change," 101 PNAS No. 25, pp. 9205-9210 at 9207-9209 (2004).
Tiwari et al, The Roles of Auxin Response Factor Domains in Auxin-Responsive Transcription, 15 The Plant Cell, pp. 533-543 (2003).
GenBank Accession No. CAF74711.1 [online], [retreived on Feb. 13, 2013], retrieved from the internet.
Cregg et al., "Recombinant Protein Expression in Pichia pastoris", 16 Molecular Biotechnology, pp. 23-52 (2000).
Han et al., "Improvement in the Reproducibility and Accuracy of DNA Microarray Quantification by Optimizing Hybridization Conditions", 7 BMC Bioinformatics Suppl 2, pp. 1-13 (2006).

Leslie van der Fits et al., ORCA3, a Jasmonate-Responsive Transcriptional Regulator of Plant Primary and Secondary Metabolism, 289 Science, pp. 295-297 (2000).
Baldwin et al., Autotoxicity and Chemical Defense: Nicotine Accumulation and Carbon Gain in Solanaceous Plants, 94 Oecologia, pp. 534-541 (1993).
Notice of Allowance dated Jun. 16, 2014, issued in related U.S. Appl. No. 12/601,752.
Notice of Allowance dated Sep. 6, 2013, issued in related U.S. Appl. No. 13/464,212.
Office Action issued in related U.S. Appl. No. 14/261,284, dated Jan. 12, 2015.
Kochevenko et al., (132 Plant Phys. Chimeric RNA/DNA Oligonucleotide-based Site-Specific Modification of the Tobacco Acetolactate Synthase Gene [Sic], pp. 174-184 (2003).
Lloyd et al., (Targeted mutagenesis using zinc-finger nucleases in *Arabidopsis*, 102 PNAS, pp. 2232-2237 (2005).
Office Action issued in related U.S. Appl. No. 14/261,132, dated Feb. 6, 2015.
Van der Fits et al., (The Jasmonate-inducible AP2/ERF-domain transcription factor ORCA3 activates gene expression via interaction with a Jasmonate-responsive promotor element, vol. 25, Plant, pp. 43-53 (2001).
Office Action issued in related U.S. Appl. No. 14/261,203, dated Dec. 19, 2014.
Office Action issued in related U.S. Appl. No. 14/261,259, dated Feb. 10, 2015.
Office Action issued in related U.S. Appl. No. 14/261,165, dated Jan. 12, 2015.
Notice of Allowance issued in related U.S. Appl. No. 14/261,240, dated Mar. 31, 2015.
Notice of Allowance issued in related U.S. Appl. No. 14/261,203, dated May 6, 2015.
Notice of Allowance issued in related U.S. Appl. No. 14/261,165, dated May 22, 2015.
Notice of Allowance issued in related U.S. Appl. No. 14/261,132, dated Jun. 5, 2015.
Notice of Allowance issued in related U.S. Appl. No. 14/261,259, dated Jun. 8, 2015.
Notice of Allowance issued in related U.S. Appl. No. 14/261,284, dated Jun. 26, 2015.
Office Action issued in related U.S. Appl. No. 14/879,456, dated Oct. 21, 2016.
Office Action issued in related U.S. Appl. No. 14/840,019, dated Jan. 23, 2017.
Office Action issued in related U.S. Appl. No. 14/852,172, dated Jan. 27, 2017.
De Sutter, et al., "Exploration of Jasmonate Signaling via Automated and Standardized Transient Expression Assays in tobacco Cells," The Plant Journal, vol. 44, pp. 1065-1076 (2005).
Corrected Notice of Allowance issued in related U.S. Appl. No. 14/879,456, dated Jun. 16, 2017.
Office Action issued in related U.S. Appl. No. 14/842,328, dated Mar. 22, 2017.
Notice of Allowance issued in related U.S. Appl. No. 14/879,456, dated Apr. 12, 2017.
Elomaa et al., "Transformation of Antisense Constructs of the Chalcone Synthase Gene Superfamily into *Gerbera hybrid*: different effect on the expression of family members," *Molecular Breeding*, vol. 2, pp. 41-50 (1996).
Sen et al., "Role of HD-Zip Transcription Factors in Plant Development and Stress Responses," *International Journ. of Agriculture, Environmental Biotechnology*, vol. 9, No. 5, pp. 711-718 (2016).
Re et al., "RNAi-mediated silencing of the HD-Zip gene HD20 in Nicotiana attenuate affects benzyl acetone emission from Corollas via ABA levels and the expression of metabolic genes," *BMC Plant Biology*, vol. 12, No. 60, pp. 1-15 (2012).
Notice of Allowance issued in related U.S. Appl. No. 14/840,019, dated May 5, 2017.
Corrected Notice of Allowance issued in related U.S. Appl. No. 14/879,456, dated May 15, 2017.
Non-Final Office Action issued in related U.S. Appl. No. 14/852,158, dated May 31, 2017.

(56) References Cited

OTHER PUBLICATIONS

Van der Fits and Memelink, The Jasmonate-Inducible AP2/ERF-domain transcription factor ORCA3 Activates Gene Expression via Interaction with a Jasmonate-Responsive Promotor Element, 25 Plant J, pp. 43-53 (2001).
Final Office Action issued in U.S. Appl. No. 14/852,172, dated May 31, 2017.
Nicotiana article. Downloaded from the web on May 25, 2017, http://en.wilkipedia.org/wilki/Nicotiana; pp. 1-3.
Chinese Office Action issued in related Chinese Patent Application No. 2015102363733, dated Jul. 31, 2017.
Boter et al., "Conserved MYC Transcription Factors Play a Key Role in Jasmonate Signaling both in Tomato and *Arabidopsis,*" *Genes & Development,* vol. 18, pp. 1577-1591 (Dec. 2004).
Notice of Allowance issued in related U.S. Appl. No. 14/842,328, dated Sep. 21, 2017.
Office Action issued in related U.S. Appl. No. 14/842,335, dated Oct. 26, 2017.
Notice of Allowance issued in related U.S. Appl. No. 14/852,158, dated Mar. 22, 2018.
Notice of Allowance issued in related U.S. Appl. No. 14/852,172, dated Jan. 24, 2018.
Office Action issued in related U.S. Appl. No. 14/852,158, dated Dec. 1, 2017.
Yadav, et al., "A Basic Helix-Loop-Helix Transcription Factor in *Arabidopsis,* MYC2, Acts as a Repressor of Blue Light-Mediated Photomorphogenic Growth," *The Plant Cell,* vol. 17, pp. 1953-1966 (Jul. 2005).
Facchini, et al., "Can *Arabidopsis* make complex alkaloids?," *Trends in Plant Science 9.3,* pp. 116-122 (2004).
Notice of Allowance issued in related U.S. Appl. No. 14/842,35, dated Jun. 11, 2018.
Office Action issued in related U.S. Appl. No. 15/658,236, dated Aug. 27, 2018.
Notice of Allowance issued in co-pending U.S. Appl. No. 15/985,146, dated Jan. 31, 2020.
Office Action issued in co-pending U.S. Appl. No. 16/041,152, dated May 14, 2020.
Office Action issued in co-pending U.S. Appl. No. 16/148,923, dated Jun. 10, 2020.
Goossens, et al., "Implementation of Functional Genomics for Gene Discovery in Alkaloid Producing Plants," *Phytochem. Rev.i,* vol. 6, pp. 35-39 (2007).
Shuilin, et al., "Plant Secondary Metabolism; Function, Regulation and Gene Engineering," *Chin. J. Appl. Environ. Biol.,* vol. 8, No. 5, pp. 558-563 (2002). [Eng. Abstract].
An Junlong, et al., "Study on Secondary Metabolite Production in Plants," *Hebei Chemical Engineering and Industry,* vol. 6, pp. 1-5 (2002). [Abstract].
Notice of Allowance issued co-pending U.S. Appl. No. 16/041,152, dated Dec. 4, 2020.

\* cited by examiner

Leaf nicotine levels in *N. benthamiana* plants transformed with constructs for overexpression or suppression of NbTF1

Leaf nicotine levels in *N. benthamiana* plants transformed with constructs for overexpression or suppression of NbTF5

NUCLEIC ACID SEQUENCES ENCODING TRANSCRIPTION FACTORS REGULATING ALKALOID BIOSYNTHESIS AND THEIR USE IN MODIFYING PLANT METABOLISM

CROSS-REFERENCE TO RELATED APPLICATIONS

This application is a divisional of U.S. patent application Ser. No. 14/681,073, filed Apr. 7, 2015, which is a divisional of U.S. patent application Ser. No. 14/261,240, filed Apr. 24, 2014, now U.S. Pat. No. 9,121,030, which is a divisional of U.S. patent application Ser. No. 12/601,752, filed Mar. 1, 2010, now U.S. Pat. No. 8,822,757, which is the U.S. National Phase of International Patent Application No. PCT/IB2008/003131, filed May 23, 2008, which claims priority from U.S. Provisional Patent Application No. 60/924,675, filed May 25, 2007. The contents of these applications are incorporated herein by reference in their entirety.

SEQUENCE LISTING

The instant application contains a Sequence Listing which has been filed electronically in ASCII format and is hereby incorporated by reference in its entirety.

FIELD OF THE INVENTION

The present invention is related to transcription factors for modifying plant metabolism, and to nucleic acid molecules that encode such transcription factors. The invention relates, inter alia, to nucleic acid sequences that encode transcription factors that regulate alkaloid production in plants, particularly but not exclusively nicotinic alkaloid production in a tobacco plant, and for producing plants and cells with altered alkaloid content.

BACKGROUND OF THE INVENTION

Many plant natural products have biological activities that make them valuable as pharmaceutical drugs. Alkaloids are a class of natural products that have proved particularly useful as drugs and medicines. Examples of biologically-active alkaloids include morphine, scopolamine, camptothecin, cocaine and nicotine. These compounds are all isolated from plant sources for use as pharmaceutical drugs. Nicotine, morphine (and related opiates) and cocaine are also addictive drugs that are responsible for significant health and societal problems worldwide.

Nicotine is a pyrrolidine alkaloid that exhibits a range of bioactivities, including potent toxicity and nervous system stimulation. In *Nicotiana tabacum, N. benthamiana* and a number of other species, nicotine is synthesized in the roots and then transported to the leaves, where it appears to play a role in defense. The biosynthesis of nicotine and many other plant metabolites can be induced by the application of a class of volatile plant hormones collectively termed jasmonates (Gundlach et al., *Proc. Natl. Acad. Sci. U.S.A.* 89: 2389-2393 (1992)). Although increases in nicotine levels can be induced by wounding or jasmonate application, the actual regulatory machinery responsible for this induction has yet to be discovered.

Plant natural product biosynthesis is mainly under transcriptional control, which allows plants to regulate metabolism in a developmental and stress-specific fashion. A number of transcription factors that regulate specific branches of secondary metabolism have been identified in plants. Anthocyanin biosynthesis is controlled by interacting MYB proteins (e.g. maize C1, *Arabidopsis* PAP1/PAP2) and basic-helix-loop-helix proteins (e.g. maize R, *petunia* AN1) (for a review see Vom Endt et al., *Phytochemistry* 61: 107-114 (2002)). Examples of other transcription factors regulating plant metabolic processes include a WRKY-type transcription factor that appears to control the transcription of a sesquiterpene synthase in cotton trichomes (Xu et al., *Plant Physiol.* 135: 507-515 (2004)) and an AP2/ERF-like transcription factor, WIN1, that up-regulates wax biosynthesis in *Arabidopsis* (Broun et al., *Curr. Opin. Plant Biol.* 7: 202-209 (2004)).

Overexpression of ORCA3 in *Catharanthus roseus* cell suspensions increased levels of transcripts of genes encoding some of the enzymes in the *C. roseus* terpenoid indole alkaloid pathway, but alkaloid accumulation was observed only when the cell suspension were provided with loganin, a terpenoid precursor. (van der Fits and Memelink. *Science* 289:295-297 (2000)). Overexpression of two transcription factors, NtORC1 and NtJAP1, increased transient expression of marker genes linked to a putrescine N-methyltransferase (PMT) promoter in tobacco cell suspensions. (De Sutter et al., *Plant J.* 44:1065-76 (2005))

SUMMARY OF THE INVENTION

In one aspect, the invention provides an isolated nucleic acid molecule comprising a nucleotide sequence selected from the group consisting of: (a) a nucleotide sequence set forth in SEQ ID NO: 1, SEQ ID NO: 2, SEQ ID NO: 4, SEQ ID NO: 5, SEQ ID NO: 6, SEQ ID NO: 8, SEQ ID NO: 9, SEQ ID NO: 11, SEQ ID NO: 12, SEQ ID NO: 14 or SEQ ID NO: 15; (b) a nucleotide sequence that encodes a polypeptide having the amino acid sequence set forth in SEQ ID NO: 3, SEQ ID NO: 7, SEQ ID NO: 10, SEQ ID NO: 13 or SEQ ID NO: 16; c) a nucleotide sequence that is at least 90% identical to the nucleotide sequences of (a) or (b), and encodes a transcription factor that regulates alkaloid biosynthesis; and (d) a nucleotide sequence that hybridizes under stringent conditions to the nucleotide sequences of (a), (b), or (c), and encodes a transcription factor that regulates alkaloid biosynthesis.

In one embodiment, there is provided a genetically engineered plant cell comprising at least 21 consecutive nucleotides of the nucleic acid sequence, wherein said consecutive nucleotides are in either sense or antisense orientation. In a further embodiment, a plant comprises the plant cell. In another further embodiment, a tissue culture comprises the plant cell, wherein said culture has enhanced production or secretion of an at least one alkaloid, alkaloid precursor, or alkaloid analog. In a further embodiment, there is a method for producing an alkaloid, alkaloid precursor, or alkaloid analog, comprising isolating said alkaloid, alkaloid precursor, alkaloid analog from the tissue culture. In one further embodiment, the tissue culture comprises a cell of a *Nicotiana* plant, such as *Nicotiana tabacum*.

In another aspect, the invention provides a recombinant transcription factor that regulates alkaloid biosynthesis having an amino acid sequence selected from the group consisting of: (a) an amino acid sequence set forth in SEQ ID NO: 3, SEQ ID NO: 7, SEQ ID NO: 10, SEQ ID NO: 13, or SEQ ID NO: 16; and (b) a variant of an amino acid sequence set forth in (a). In one embodiment, the alkaloid is a nicotinic alkaloid. In a further embodiment, the nicotinic alkaloid is nicotine. In another embodiment, the plant belongs to the genus *Nicotiana*. In a further embodiment, the plant is *Nicotiana tabacum*. In another embodiment, the method provides a reduced alkaloid plant. In a further embodiment, a reduced alkaloid product is produced from the reduced alkaloid plant.

In another aspect, there is provided a method for reducing an alkaloid in a plant, comprising down-regulating a transcription factor that positively regulates alkaloid biosynthesis. In one embodiment, the transcription factor is down-regulated by (a) introducing into the plant a nucleotide sequence comprising i) at least 21 consecutive nucleotides of a sequence selected from the group of SEQ ID NO: 1, SEQ ID NO: 5, SEQ ID NO: 8, or SEQ ID NO: 11, wherein said consecutive nucleotides are in either sense or antisense orientation; and (b) growing the plant under conditions whereby said nucleotide sequence decreases levels of the transcription factor in the plant compared to a control plant grown under similar conditions. In one embodiment, the alkaloid is a nicotinic alkaloid. In a further embodiment, the nicotinic alkaloid is nicotine. In another embodiment, the plant belongs to the genus *Nicotiana*. In a further embodiment, the plant is *Nicotiana tabacum*. In another embodiment, the method provides a reduced alkaloid plant. In a further embodiment, a reduced alkaloid product is produced from the reduced alkaloid plant.

In another aspect, the invention provides a method for reducing alkaloid levels in a population of plants, comprising: (a) providing a population of mutated plants; (b) detecting and selecting a target mutated plant within said population, wherein said target mutated plant has decreased expression of a transcription factor that positively regulates alkaloid biosynthesis compared to a control plant; and (c) selectively breeding the target mutated plant to produce a population of plants having decreased expression of a transcription factor that positively regulates alkaloid biosynthesis compared to a population of control plants. In one embodiment, the detecting comprises using primers developed from SEQ ID NO: 1, SEQ ID NO: 5, SEQ ID NO: 8, or SEQ ID NO: 11 to amplify regions of the transcription factor gene from mutated plants in the population of mutated plants, identifying mismatches between the amplified regions and corresponding regions in wild-type gene that lead to the decreased expression of a transcription factor that positively regulates alkaloid biosynthesis, and identifying the mutated plant that contains the mismatches. In one embodiment, the alkaloid is a nicotinic alkaloid. In a further embodiment, the nicotinic alkaloid is nicotine. In another embodiment, the plant belongs to the genus *Nicotiana*. In a further embodiment, the plant is *Nicotiana tabacum*. In another embodiment, the method provides a reduced alkaloid plant. In a further embodiment, a reduced alkaloid product is produced from the reduced alkaloid plant.

In another aspect, the invention provides a method for reducing an alkaloid in a plant, comprising up-regulating a transcription factor that negatively regulates alkaloid biosynthesis. In one embodiment, the transcription factor is up-regulated by (a) introducing into the plant an expression construct comprising a nucleotide sequence selected from the group of SEQ ID NO: 4, SEQ ID NO: 14, or SEQ ID NO: 15; and (b) growing the plant under conditions whereby said expression construct increases levels of the transcription factor in the plant compared to a control plant grown under similar conditions. In one embodiment, the alkaloid is a nicotinic alkaloid. In a further embodiment, the nicotinic alkaloid is nicotine. In another embodiment, the plant belongs to the genus *Nicotiana*. In a further embodiment, the plant is *Nicotiana tabacum*. In another embodiment, the method provides a reduced alkaloid plant. In a further embodiment, a reduced alkaloid product is produced from the reduced alkaloid plant.

In another aspect, the invention provides a method for reducing a nicotinic alkaloid in a plant, comprising down-regulating a transcription factor that positively regulates alkaloid biosynthesis and down-regulating at least one of NBB1, A622, QPT, PMT, and MPO. In one embodiment, the nicotinic alkaloid is nicotine. In another embodiment, the plant belongs to the genus *Nicotiana*. In a further embodiment, the plant is *Nicotiana tabacum*. In another embodiment, the method provides a reduced alkaloid plant. In a further embodiment, a reduced alkaloid product is produced from the reduced alkaloid plant.

In another aspect, the invention provides a method for reducing a nicotinic alkaloid in a plant, comprising up-regulating a transcription factor that negatively regulates alkaloid biosynthesis and down-regulating at least one of NBB1, A622, QPT, PMT, and MPO. In one embodiment, the nicotinic alkaloid is nicotine. In another embodiment, the plant belongs to the genus *Nicotiana*. In a further embodiment, the plant is *Nicotiana tabacum*. In another embodiment, the method provides a reduced alkaloid plant. In a further embodiment, a reduced alkaloid product is produced from the reduced alkaloid plant.

In another aspect, the invention provides a method for increasing an alkaloid in a plant, comprising down-regulating a transcription factor that negatively regulates alkaloid biosynthesis. In one embodiment, the transcription factor is down-regulated by (a) introducing into the plant a nucleotide sequence comprising i) at least 21 consecutive nucleotides of a sequence selected from the group of SEQ ID NO: 4 and SEQ ID NO: 14, wherein said consecutive nucleotides are in either sense or antisense orientation; and (b) growing the plant under conditions whereby said nucleotide sequence decreases levels of the transcription factor in the plant compared to a control plant grown under similar conditions. In one embodiment, the alkaloid is a nicotinic alkaloid. In another embodiment, the plant belongs to the genus *Nicotiana*. In a further embodiment, the plant is *Nicotiana tabacum*. In another embodiment, the method produces an increased alkaloid plant. In a further embodiment, an increased alkaloid product is produced from the plant. In a still further embodiment, the increased alkaloid is nicotine.

In another aspect, the invention provides a method for increasing alkaloid levels in a population of plants, comprising: (a) providing a population of mutated plants; (b) detecting and selecting a target mutated plant within said population, wherein said target mutated plant has decreased expression of a transcription factor that negatively regulates alkaloid biosynthesis compared to a control plant; and (c) selectively breeding the target mutated plant to produce a population of plants having decreased expression of a transcription factor that negatively regulates alkaloid biosynthesis compared to a population of control plants. In one embodiment, the detecting comprising using primers developed from SEQ ID NO: 4 or SEQ ID NO: 14 to amplify regions of the transcription factor gene from mutated plants in the population of mutated plants, identifying mismatches between the amplified regions and corresponding regions in wild-type gene that lead to the decreased expression of a transcription factor that negatively regulates alkaloid biosynthesis, and identifying the mutated plant that contains the mismatches. In one embodiment, the alkaloid is a nicotinic alkaloid. In another embodiment, the plant belongs to the genus *Nicotiana*. In a further embodiment, the plant is *Nicotiana tabacum*. In another embodiment, the method produces an increased alkaloid plant. In a further embodiment, an increased alkaloid product is produced from the plant. In a still further embodiment, the increased alkaloid is nicotine.

In another aspect, the invention provides a method for increasing an alkaloid in a plant, comprising up-regulating a transcription factor that positively regulates alkaloid biosynthesis. In one embodiment, the transcription factor is up-regulated by (a) introducing into the plant a expression construct comprising a nucleotide sequence selected from the group of SEQ ID NO: 2, SEQ ID NO: 6, SEQ ID NO: 9, SEQ ID NO: 12 or SEQ ID NO: 15; and (b) growing the plant under conditions whereby said expression construct increases levels of the transcription factor in the plant compared to a control plant grown under similar conditions. In one embodiment, the alkaloid is a nicotinic alkaloid. In another embodiment, the plant belongs to the genus *Nicotiana*. In a further embodiment, the plant is *Nicotiana tabacum*. In another embodiment, the method produces an increased alkaloid plant. In a further embodiment, an increased alkaloid product is produced from the plant. In a still further embodiment, the increased alkaloid is nicotine.

In another aspect, there is provided a method for increasing a nicotinic alkaloid in a plant, comprising down-regulating a transcription factor that negatively regulates alkaloid biosynthesis and up-regulating at least one of NBB1, A622, QPT, PMT and MPO. In one embodiment, the plant belongs to the genus *Nicotiana*. In a further embodiment, the plant is *Nicotiana tabacum*. In another embodiment, the nicotinic alkaloid is nicotine. In another embodiment, the method produces an increased alkaloid plant. In a further embodiment, an increased alkaloid product is produced from the plant. In a still further embodiment, the increased alkaloid is nicotine.

In another aspect, there is provided a method for increasing a nicotinic alkaloid in a plant, comprising up-regulating a transcription factor that positively regulates alkaloid biosynthesis and up-regulating at least one of NBB1, A622, QPT, PMT and MPO. In one embodiment, the plant belongs to the genus *Nicotiana*. In a further embodiment, the plant is *Nicotiana tabacum*. In another embodiment, the nicotinic alkaloid is nicotine. In another embodiment, the method produces an increased alkaloid plant. In a further embodiment, an increased alkaloid product is produced from the plant. In a still further embodiment, the increased alkaloid is nicotine.

DETAILED DESCRIPTION OF THE INVENTION

Figure 1:
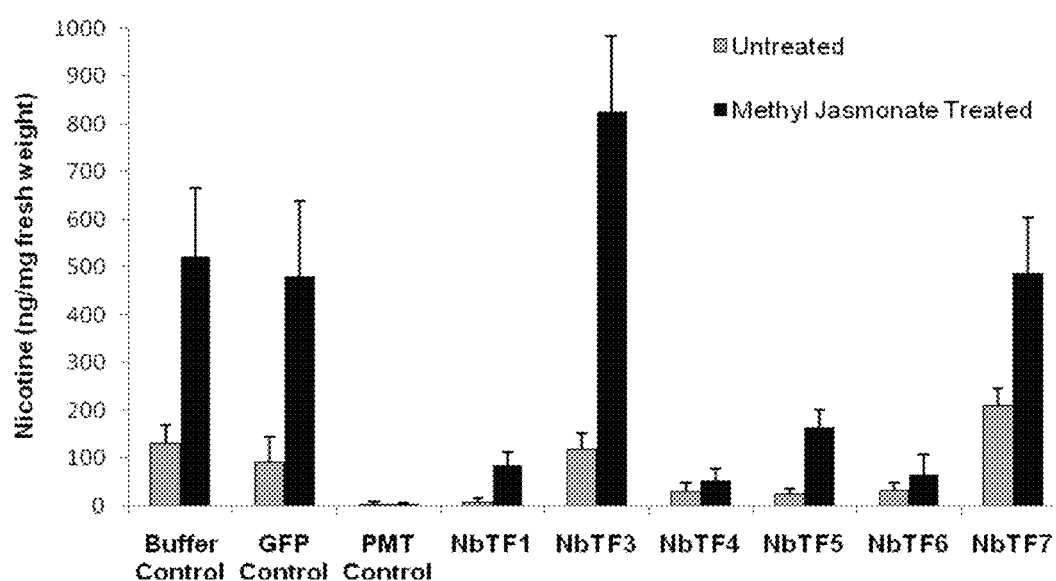
FIG. 1 depicts leaf nicotine levels in control and VIGS silenced *N. benthamiana* plants.

The present inventors have identified six genes encoding transcription factors that regulate the nicotinic alkaloid biosynthetic pathway. The nucleic acid sequences of the genes have been determined. The full-length sequence of the NbTF1 gene is set forth in SEQ ID NO: 1. The open reading frame (ORF) of SEQ ID NO: 1, set forth in SEQ ID NO: 2, encodes the polypeptide sequence set forth in SEQ ID NO: 3. The sequence of a portion of the NbTF3 gene, which includes the fragment used for VIGS, is set forth in SEQ ID NO: 4. The full-length sequence of the NbTF4 gene, including some sequence that is upstream of the transcriptional start site, is set forth in SEQ ID NO: 5. The ORF of SEQ ID NO: 5, set forth in SEQ ID NO: 6, encodes the polypeptide sequence set forth in SEQ ID NO: 7. The full-length sequence of the NbTF5 gene is set forth in SEQ ID NO: 8. The ORF of SEQ ID NO: 8, set forth in SEQ ID NO: 9, encodes the polypeptide sequence set forth in SEQ ID NO: 10. The full-length sequence of the NbTF6 gene is set forth in SEQ ID NO: 11. The ORF of SEQ ID NO: 11, set forth in SEQ ID NO: 12, encodes the polypeptide sequence set forth in SEQ ID NO: 13. The full-length sequence of the NbTF7 gene is set forth in SEQ ID NO: 14. The ORF of SEQ ID NO: 14, set forth in SEQ ID NO: 15, encodes the polypeptide sequence set forth in SEQ ID NO: 16.

NbTF1, NbTF4, NbTF5. and NbTF6 positively regulates on alkaloid biosynthesis. NbTF3 and NbTF7 negatively regulate alkaloid biosynthesis. The transcription factors belong to several different classes of transcription factors known from plants: NbTF1, NbTF3 and NbTF5 are Myc, basic helix-loop-helix transcription factors; NbTF4 is a homeodomain leucine zipper transcription factor; NbTF6 is an AP2, ethylene-response factor; and NbTF7 is a B3 domain, auxin response factor.

These transcription factor genes or fragments thereof may be used to suppress synthesis of alkaloids (e.g., of nicotinic alkaloids) in plants that naturally produce the alkaloids. For example, *Nicotiana* spp. (e.g. *N. tabacum, N. rustica* and *N. benthamiana*) naturally produce nicotinic alkaloids. *N. tabacum* is an agricultural crop of high productivity and biotechnological uses of this plant continue to increase. Reducing nicotine biosynthesis genetic engineering of transcription factor expression leads to creating tobacco varieties that contain zero or low nicotine levels for use as low-toxicity production platforms for the production of plant-made pharmaceuticals (PMPs) (e.g. recombinant proteins and antibodies) or as industrial, food and biomass crops. The transcription factor genes or fragments thereof may be used in plants or plant cells to increase synthesis of alkaloids (e.g., of nicotinic alkaloids) and related compounds, which may have therapeutic applications.

Definitions

All technical terms employed in this specification are commonly used in biochemistry, molecular biology and agriculture; hence, they are understood by those skilled in the field to which this invention belongs. Those technical terms can be found, for example in: MOLECULAR CLONING: A LABORATORY MANUAL 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (including periodic updates); SHORT PROTOCOLS IN MOLECULAR BIOLOGY: A COMPENDIUM OF METHODS FROM CURRENT PROTOCOLS IN MOLECULAR BIOLOGY 5th ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997. Methodology involving plant biology techniques are described here and also are described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995.

By "isolated nucleic acid molecule" is intended a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules, according to the present invention, further include such molecules produced synthetically.

A "chimeric nucleic acid" comprises a coding sequence or fragment thereof linked to a nucleotide sequence that is different from the nucleotide sequence with which it is associated in cells in which the coding sequence occurs naturally.

"Heterologous nucleic acid" refers to a nucleic acid, DNA or RNA, which has been introduced into a cell (or the cell's ancestor) which is not a copy of a sequence naturally found in the cell into which it is introduced. Such heterologous nucleic acid may comprise segments that are a copy of a sequence which is naturally found in the cell into which it has been introduced, or fragments thereof.

"Endogenous nucleic acid" or "endogenous sequence" is "native" to, i.e., indigenous to, the plant or organism that is to be genetically engineered. It refers to a nucleic acid, gene, polynucleotide, DNA, RNA, mRNA, or cDNA molecule that is present in the genome of a plant or organism that is to be genetically engineered.

"Exogenous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein.

"Sequence identity" or "identity" in the context of two polynucleotide (nucleic acid) or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties, such as charge and hydrophobicity, and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers & Miller, *Computer Applic. Biol. Sci.* 4: 11-17 (1988), as implemented in the program PC/GENE (Intelligenetics, Mountain View, Calif., USA).

Use in this description of a percentage of sequence identity denotes a value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A "variant" is a nucleotide or amino acid sequence that deviates from the standard, or given, nucleotide or amino acid sequence of a particular gene or polypeptide. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a variant sequence. A polypeptide variant may have "conservative" changes, wherein a substituted amino acid has similar structural or chemical properties, e.g., replacement of leucine with isoleucine. A polypeptide variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. Variant may also refer to a "shuffled gene" such as those described in Maxygen-assigned patents (e.g. U.S. Pat. No. 6,602,986).

"Genetic engineering" encompasses any methodology for introducing a nucleic acid or specific mutation into a host organism. For example, a plant is genetically engineered when it is transformed with a polynucleotide sequence that suppresses expression of a gene, such that expression of a target gene is reduced compared to a control plant. A plant is genetically engineered when a polynucleotide sequence is introduced that results in the expression of a novel gene in the plant, or an increase in the level of a gene product that is naturally found in the plants. In the present context, "genetically engineered" includes transgenic plants and plant cells, as well as plants and plant cells produced by means of targeted mutagenesis effected, for example, through the use of chimeric RNA/DNA oligonucleotides, as described by Beetham et al., *Proc. Natl. Acad. Sci. U.S.A.* 96: 8774-8778 (1999) and Zhu et al., *Proc. Natl. Acad. Sci. U.S.A.* 96: 8768-8773 (1999), or so-called "recombinagenic olionucleobases," as described in International patent publication WO 2003/013226. Likewise, a genetically engineered plant or plant cell may be produced by the introduction of a modified virus, which, in turn, causes a genetic modification in the host, with results similar to those produced in a transgenic plant, as described herein. See, e.g., U.S. Pat. No. 4,407,956. Additionally, a genetically engineered plant or plant cell may be the product of any native approach (i.e., involving no foreign nucleotide sequences), implemented by introducing only nucleic acid sequences derived from the host plant species or from a sexually compatible plant species. See, e.g., U.S. published patent application No. 2004/0107455.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, operably linked means that the nucleic acid sequences being linked are contiguous.

As used herein, "expression" denotes the production of an RNA product through transcription of a gene or the production of the polypeptide product encoded by a nucleotide sequence. "Overexpression" or "up-regulation" is used to indicate that expression of a particular gene sequence or variant thereof, in a cell or plant, including all progeny plants derived thereof, has been increased by genetic engineering, relative to a control cell or plant (e.g., "NbTF1 overexpression").

The terms "suppression" or "down-regulation" are used synonymously to indicate that expression of a particular gene sequence variant thereof, in a cell or plant, including all progeny plants derived thereof, has been reduced by genetic engineering, relative to a control cell or plant (e.g., "NbTF1 down-regulation").

A "transcription factor" is a protein that binds that binds to DNA regions, typically promoter regions, using DNA binding domains and increases or decreases the transcription of specific genes. A transcription factor "positively regulates" alkaloid biosynthesis if expression of the transcription factor increases the transcription of one or more genes encoding alkaloid biosynthesis enzymes and increases alkaloid production. A transcription factor "negatively regulates" alkaloid biosynthesis if expression of the transcription factor decreases the transcription of one or more genes encoding alkaloid biosynthesis enzymes and decreases alkaloid production. Transcription factors are classified based on the similarity of their DNA binding domains. (see, e.g. Stegmaier et al., *Genome Inform.* 15 (2): 276-86 ((2004)). Classes of plant transcription factors include Myc basic helix-loop-helix transcription factors; homeodomain leucine zipper transcription factors; AP2 ethylene-response factor transcription factors; and B3 domain, auxin response factor transcription factors.

An "alkaloid" is a nitrogen-containing basic compound found in plants and produced by secondary metabolism. A "pyrrolidine alkaloid" is an alkaloid containing a pyrrolidine ring as part of its molecular structure, for example, nicotine. Nicotine and related alkaloids are also referred to as pyridine alkaloids in the published literature. A "pyridine alkaloid" is an alkaloid containing a pyridine ring as part of its molecular structure, for example, nicotine. A "nicotinic alkaloid" is nicotine or an alkaloid that is structurally related to nicotine and that is synthesized from a compound produced in the nicotine biosynthesis pathway. Illustrative nicotinic alkaloids include but are not limited to nicotine, nornicotine, anatabine, anabasine, anatalline, N-methylanatabine, N-methylanabasine, myosmine, anabaseine, formylnornicotine, nicotyrine, and cotinine. Other very minor nicotinic alkaloids in tobacco leaf are reported, for example, in Hecht et al., *Accounts of Chemical Research* 12: 92-98 (1979); Tso, T. G., *Production, Physiology and Biochemistry of Tobacco Plant*. Ideals Inc., Beltsville, Mo. (1990).

As used herein "alkaloid content" means the total amount of alkaloids found in a plant, for example, in terms of pg/g dry weight (DW) or ng/mg fresh weight (FW). "Nicotine content" means the total amount of nicotine found in a plant, for example, in terms of mg/g DW or FW.

"Plant" is a term that encompasses whole plants, plant organs (e. g. leaves, stems, roots, etc.), seeds, differentiated or undifferentiated plant cells, and progeny of the same. Plant material includes without limitation seeds, suspension cultures, embryos, meristematic regions, callus tissues, leaves, roots, shoots, stems, fruit, gametophytes, sporophytes, pollen, and microspores.

"Tobacco" or "tobacco plant" refers to any species in the *Nicotiana* genus that produces nicotinic alkaloids, including but are not limited to the following: *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana hybrid, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana tabacum, Nicotiana thyrsiflora, Nicotiana tomentosa, Nicotiana tomentosifomis, Nicotiana trigonophylla, Nicotiana umbratica, Nicotiana undulata, Nicotiana velutina, Nicotiana wigandioides*, and interspecific hybrids of the above.

"Tobacco product" refers to a product comprising material produced by a *Nicotiana* plant, including for example, nicotine gum and patches for smoking cessation, cigarette tobacco including expanded (puffed) and reconstituted tobacco, cigar tobacco, pipe tobacco, cigarettes, cigars, and all forms of smokeless tobacco such as chewing tobacco, snuff, snus and lozenges.

"Decreased alkaloid plant' or "reduced alkaloid plant" encompasses a genetically engineered plant that has a decrease in alkaloid content to a level less than 50%, and preferably less than 10%, 5%, or 1% of the alkaloid content of a control plant of the same species or variety.

"Increased alkaloid plant" encompasses a genetically engineered plant that has an increase in alkaloid content greater than 10%, and preferably greater than 50%, 100%, or 200% of the alkaloid content of a control plant of the same species or variety.

I. Reducing Alkaloid Production in Plants

A. Decreasing Alkaloids by Suppressing a Transcription Factor that Positively Regulates Alkaloid Production.

Alkaloid (e.g. nicotine) production may be reduced by suppression of an endogenous gene encoding a transcription factor that positively regulates alkaloid production using the transcription factor gene sequences of the present invention in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques. Accordingly, the present invention provides methodology and constructs for decreasing alkaloid content in a plant, by suppressing a gene encoding a transcription factor that positively regulates alkaloid production, such as NbTF1, NbTF4, NbTF5, and NbTF6. Suppressing more than one gene encoding a transcription factor that positively regulates on alkaloid production may further decrease alkaloids levels in a plant.

B. Decreasing Alkaloids by Suppressing a Transcription Factor that Positively Regulates Alkaloid Production and at Least One Alkaloid Biosynthesis Gene.

Previous reports indicate that suppressing an alkaloid biosynthesis gene in *Nicotiana* decreases nicotinic alkaloid content. For example, suppressing QPT reduces nicotine levels. (see U.S. Pat. No. 6,586,661). Suppressing A622 or NBB1 also reduces nicotine levels (see International patent publication WO 2006/109197), as does suppressing PMT (see Chintapakorn and Hamill. *Plant Mol. Biol.* 53:87-105 (2003)) or MPO (see International patent publications WO 2008/020333 and 2008/008844; Katoh et al., *Plant Cell Physiol.* 48(3): 550-4 (2007)). Accordingly, the present invention contemplates further decreasing nicotinic alkaloid content by suppressing one or more of A622, NBB1, QPT, PMT and MPO and suppressing a transcription factor that positively regulates alkaloid production. Pursuant to this aspect of the invention, a nucleic acid construct comprising at least a fragment of one or more of NbTF1, NbTF4, NbTF5, and NbTF6 and at least a fragment one or more of A622, NBB1, QPT, PMT, and MPO are introduced into a cell or plant. An illustrative nucleic acid construct may comprise both a fragment of NbTF1 and QPT.

C. Decreasing Alkaloids by Overexpressing a Transcription Factor with a Negative Regulatory Effect on Alkaloid Production.

Alkaloid (e.g. nicotine) production may be reduced by overexpression of a gene encoding a transcription factor that negatively regulates alkaloid production using the transcription factor gene sequences of the present invention in a number of ways generally known in the art. Accordingly, the present invention provides methodology and constructs for decreasing alkaloid content in a plant, by overexpressing a gene encoding a transcription factor that negatively regulates alkaloid production, such as NbTF3 or NbTF7. Overexpressing more than one gene encoding a transcription factor that negatively regulates alkaloid production may further decrease alkaloids levels in a plant.

D. Decreasing Alkaloids by Overexpressing a Transcription Factor that Negatively Regulates Alkaloid Production and Suppression at Least One Alkaloid Biosynthesis Gene.

As described in (I)(B) above, it is known that nicotinic alkaloid content can be decreased by suppressing an alkaloid biosynthesis gene. Accordingly, the present invention contemplates further decreasing nicotinic alkaloid content by suppressing one or more of A622, NBB1, QPT, PMT and MPO and overexpressing a transcription factor with a negative regulatory effect on alkaloid production. Pursuant to this aspect of the invention, a nucleic acid construct comprising one or more of NbTF3 or NbTF7 or their ORFs and at least a fragment of one or more of A622, NBB1, QPT, PMT, and MPO are introduced into a cell or plant. An illustrative nucleic acid construct may comprise both the NbTF3 ORF and at least a fragment of QPT.

E. Decreasing Alkaloids by Suppressing a Transcription Factor that Negatively Regulates Alkaloid Production and Overexpressing a Transcription Factor that Positively Regulates Alkaloid Production.

The present invention further contemplates decreasing nicotinic alkaloid content by suppressing one or more of NbTF1, NbTF4, NbTF5, and NbTF6 and overexpressing one or more of NbTF3 or NbTF7.

II. Increasing Alkaloid Production

A. Increasing Alkaloids by Overexpressing a Transcription Factor that Positively Regulates Alkaloid Production.

The present invention also relates to increasing alkaloids in plants by overexpressing a transcription factor with a positive regulatory effect on alkaloid production. One or more of the NbTF1, NbTF4, NbTF5, and NbTF6 genes or their open reading frames may be used to engineer overproduction of alkaloids, for example nicotinic alkaloids (e.g. nicotine) in plants or plant cells.

B. Increasing Alkaloids by Overexpressing a Transcription Factor that Positively Regulates Alkaloid Production and at Least One at Least One Alkaloid Biosynthesis Gene.

Alkaloids, such as nicotine, can be increased by overexpressing one or more genes encoding enzymes in the alkaloid biosynthesis pathway. See for example Sato et al. *Proc. Natl. Acad. Sci. U.S.A.* 98(1):367-72 (2001). The effect of overexpressing PMT alone on nicotine content of leaves was an increase of only 40% despite 4- to 8-fold increases in PMT transcript levels in roots, suggesting that limitations at other steps of the pathway prevented a larger effect. Therefore, the present invention contemplates that overexpressing a transcription factor with a positive regulatory effect on alkaloid production and at least one at least one alkaloid biosynthesis gene, such as PMT, will result in greater alkaloid production than up-regulating the alkaloid biosynthesis gene alone.

Pursuant to this aspect of the invention, a nucleic acid construct comprising one or more of NbTF1, NbTF4, NbTF5, and NbTF6 genes or their open reading frames and at least one of A622, NBB1, QPT, PMT, and MPO is introduced into a plant cell. An illustrative nucleic acid construct may comprise, for example, both NbTF1 and PMT. Similarly, for example, a genetically engineered plant overexpressing NbTF1 and PMT may be produced by crossing a transgenic plant overexpressing NbTF1 with a transgenic plant overexpressing PMT. Following successive rounds of crossing and selection, a genetically engineered plant overexpressing NbTF1 and PMT can be selected.

C. Increasing Alkaloids by Suppressing a Transcription Factor that Negatively Regulates Alkaloid Production.

Alkaloid (e.g. nicotine) production may be increased by suppression of a gene encoding a transcription factor that negatively regulates alkaloid production using the transcription factor gene sequences of the present invention in a number of ways generally known in the art. Accordingly, the present invention provides methodology and constructs for increasing alkaloid content in a plant, by suppressing a gene encoding a transcription factor that negatively regulates alkaloid production, such as NbTF3 or NbTF7. Suppressing more than one gene encoding a transcription factor that negatively regulates alkaloid production may further increase alkaloids levels in a plant.

D. Increasing Alkaloids by Suppressing a Transcription Factor that Negatively Regulates Alkaloid Production and Overexpressing at Least One Alkaloid Biosynthesis Gene.

As described in (II)(B) above, it is known that nicotinic alkaloid content can be increased by overexpressing an alkaloid biosynthesis gene. Accordingly, the present invention contemplates further increasing nicotinic alkaloid content by overexpressing one or more of A622, NBB1, QPT, PMT and MPO and suppressing a transcription factor with a negative regulatory effect on alkaloid production. Pursuant to this aspect of the invention, a nucleic acid construct comprising at least a fragment of NbTF3 or NbTF7 and one or more of A622, NBB1, QPT, PMT, and MPO are introduced into a cell or plant. An illustrative nucleic acid construct may comprise both a fragment of NbTF3 and QPT.

E. Increasing Alkaloids by Overexpressing a Transcription Factor that Positively Regulates Alkaloid Production and Suppressing a Transcription Factor that Negatively Regulates Alkaloid Production.

The present invention further contemplates increasing nicotinic alkaloid content by overexpressing one or more of NbTF1, NbTF4, NbTF5, and NbTF6 and suppressing one or more of NbTF3 or NbTF7.

III. Altering Content of Minor Alkaloids, Alkaloid Precursors, and Related Compounds It is known that suppression of an alkaloid biosynthesis gene can increase the accumulation of precursor compounds or increase the relative content of minor alkaloids. For example, suppression of PMT in *N. tabacum* resulted in an increase in anatabine. (Chintapakorn and Hamill. *Plant Mol. Biol.* 53:87-105 (2003)) Suppression of a cytochrome P450 (littorine hydroxylase/mutase) involved in tropane alkaloid biosynthesis in *Hyoscyamus niger* resulted in accumulation of the intermediate littorine, which immediately precedes the blocked step (Li et al., *Chem. Biol.* 13:513-20 (2006)). Up-regulation of the alkaloid pathway by overexpression of a transcription factor that positively regulates alkaloid production or suppression of a transcription factor that negatively regulates alkaloid production, while also suppressing an alkaloid biosynthesis gene can result in a further increase in minor alkaloid, alkaloid precursor, or related compound. Pursuant to this aspect of the invention, a nucleic acid construct comprising one or more of NbTF1, NbTF4, NbTF5, and NbTF6 or their open reading frames and at least a fragment of one of A622, NBB1, QPT, PMT, and MPO is introduced into a plant cell. Alternatively, a nucleic acid construct comprising at least a fragment of NbTF3 or NbTF7 and at least a fragment of one or more of A622, NBB1, QPT, PMT, and MPO are introduced into a cell or plant. An illustrative nucleic acid construct may comprise both a fragment of NbTF3 and a fragment of PMT.

IV. Genetic Engineering of Plants and Cells Using Transcription Factor Sequences that Regulate Alkaloid Production Transcription Factor Sequences Transcription factor genes have been identified in several plant species, exemplified by *Nicotiana* plants. Accordingly, the present invention embraces any nucleic acid, gene, polynucleotide, DNA, RNA, mRNA, or cDNA molecule that is isolated from the genome of a plant species, or produced synthetically, that encodes a transcription factor that regulates alkaloid biosynthesis. The DNA or RNA may be double-stranded or single-stranded. Single-stranded DNA may be the coding strand, also known as the sense strand, or it may be the non-coding strand, also called the anti-sense strand.

It is understood to one skilled in the art that transcription factor genes of the present invention include the sequences set forth in SEQ ID NO: 1, SEQ ID NO: 4, SEQ ID NO:5, SEQ ID NO: 8, SEQ ID NO: 11, SEQ ID NO: 14 and SEQ ID NO: 15, including fragments thereof at least about 21 consecutive nucleotides, which are of a sufficient length as to be useful in induction of gene silencing in plants (Hamilton and Baulcombe, Science 286, 950-952 (1999)).

The invention includes as well as nucleic acid molecules comprised of "variants" of SEQ ID NO: 1, SEQ ID NO: 4, SEQ ID NO: 5, SEQ ID NO: 8, SEQ ID NO: 11, SEQ ID NO: 14, and SEQ ID NO: 15, with one or more bases deleted, substituted, inserted, or added, which variant codes for a polypeptide that regulates alkaloid biosynthesis activity. Accordingly, sequences having "base sequences with one or more bases deleted, substituted, inserted, or added" retain physiological activity even when the encoded amino acid sequence has one or more amino acids substituted, deleted, inserted, or added. Additionally, multiple forms of transcription factors NbTF1, NbTF3, NbTF4, NbTF5, NbTF6 and NbTF7 may exist, which may be due to post-translational modification of a gene product, or to multiple forms of the transcription factor gene. Nucleotide sequences that have such modifications and that code for a transcription factor that regulates alkaloid biosynthesis are included within the scope of the present invention.

For example, the poly A tail or 5'- or 3'-end, nontranslated regions may be deleted, and bases may be deleted to the extent that amino acids are deleted. Bases may also be substituted, as long as no frame shift results. Bases also may be "added" to the extent that amino acids are added. It is essential, however, that any such modification does not result in the loss of transcription factor activity that regulates alkaloid biosynthesis. A modified DNA in this context can be obtained by modifying the DNA base sequences of the invention so that amino acids at specific sites in the encoded polypeptide are substituted, deleted, inserted, or added by site-specific mutagenesis, for example. (see Zoller & Smith, *Nucleic Acid Res.* 10: 6487-500 (1982)).

A transcription factor sequence can be synthesized ab initio from the appropriate bases, for example, by using an appropriate protein sequence disclosed herein as a guide to create a DNA molecule that, though different from the native DNA sequence, results in the production of a protein with the same or similar amino acid sequence.

Unless otherwise indicated, all nucleotide sequences determined by sequencing a DNA molecule herein were determined using an automated DNA sequencer, such as the Model 3730x1 from Applied Biosystems, Inc. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

For the purpose of the invention, two sequences hybridize under stringent conditions when they form a double-stranded complex in a hybridization solution of 6×SSE, 0.5% SDS, 5×Denhardt's solution and 100 μg of non-specific carrier DNA. See Ausubel et al., supra, at section 2.9, supplement 27 (1994). Sequences may hybridize at "moderate stringency," which is defined as a temperature of 60° C. in a hybridization solution of 6×SSE, 0.5% SDS, 5×Denhardt's solution and 100 μg of non-specific carrier DNA. For "high stringency" hybridization, the temperature is increased to 68° C. Following the moderate stringency hybridization reaction, the nucleotides are washed in a solution of 2×SSE plus 0.05% SDS for five times at room temperature, with subsequent washes with 0.1×SSC plus 0.1% SOS at 60° C. for 1 h. For high stringency, the wash temperature is increased to 68° C. For the purpose of the invention, hybridized nucleotides are those that are detected using 1 ng of a radiolabeled probe having a specific radio-activity of 10,000 cpm/ng, where the hybridized nucleotides are clearly visible following exposure to X-ray film at −70° C. for no more than 72 hours.

The present application is directed to such nucleic acid molecules which are at least 60%, 65%, 70%, 75%, 80%, 85%, 90%, 95%, 96%, 97%, 98%, 99% or 100% identical to a nucleic acid sequence described in any of SEQ ID NO: 1-2. Preferred are nucleic acid molecules which are at least 95%, 96%, 97%, 98%, 99% or 100% identical to the nucleic acid sequence shown in any of SEQ ID NO: 1, SEQ ID NO: 2, SEQ ID NO: 4, SEQ ID NO: 5, SEQ ID NO:6, SEQ ID NO: 8, SEQ ID NO: 9, SEQ ID NO: 11, SEQ ID NO: 12, SEQ ID NO: 14, and SEQ ID NO: 15. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 85%, 90%, 95%, 96%, 97%, 98% or 99% identical to a reference nucleotide sequence refers to a comparison made between two molecules using standard algorithms well known in the art and can be determined conventionally using publicly available computer programs such as the BLASTN algorithm. See Altschul et al., *Nucleic Acids Res.* 25: 3389-402 (1997).

The present invention further provides nucleic acid molecules comprising the nucleotide sequence of SEQ ID NO: 1, SEQ ID NO: 2, SEQ ID NO: 4, SEQ ID NO: 5, SEQ ID NO:6, SEQ ID NO: 8, SEQ ID NO: 9, SEQ ID NO: 11, SEQ ID NO: 12, SEQ ID NO: 14, and SEQ ID NO: 15, which encode a transcription factor polypeptide, wherein the polypeptide has an amino acid sequence that corresponds to SEQ ID NO: 3, SEQ ID NO: 7, SEQ ID NO: 10, SEQ ID NO: 13, or SEQ ID NO: 16, and wherein the polypeptide of the invention encompasses amino acid substitutions, additions and deletions that do not alter the function of the transcription factor polypeptide.

Methodology for Suppressing a Transcription Factor that Regulates Alkaloid Production In one aspect of the invention, methods and constructs are provided for suppressing a transcription factor that regulates alkaloid production, altering alkaloid levels, and producing plants with altered alkaloid levels. While any method may be used for suppressing a transcription factor that regulates alkaloid production, the present invention contemplates antisense, sense co-suppression, RNAi, artificial microRNA, virus-induced gene silencing (VIGS), antisense, sense co-suppression, and targeted mutagenesis approaches.

RNAi techniques involve stable transformation using RNAi plasmid constructs (Helliwell and Waterhouse, *Methods Enzymol.* 392:24-35 (2005)). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab et al., *Plant Cell* 18:1121-33 (2006); Alvarez et al, *Plant Cell* 18:1134-51 (2006)). In this method, 21 nucleotide long fragments of the gene to be silenced are introduced into a pre-miRNA gene to form a pre-amiRNA construct. The pre-miRNA construct is transferred into the plant genome using transformation methods apparent to one skilled in the art. After transcription of the pre-amiRNA, processing yields amiRNAs that target genes, which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous-antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used. Tobacco rattle virus based VIGS systems are described for example, in Baulcombe, *Curr. Opin. Plant Biol.* 2: 109-113 (1999); Lu, et al., *Methods* 30: 296-303 (2003); Ratcliff, et al., *The Plant Journal* 25: 237-245 (2001); and U.S. Pat. No. 7,229,829.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail in Stam et al., Plant J. 21:27-42 (2000).

Sense co-suppression techniques involve introducing a highly expressed sense transgene into a plant resulting in reduced expression of both the transgene and the endogenous gene (Depicker and van Montagu, Curr. Opin. Cell Biol. 9: 373-82 (1997)). The effect depends on sequence identity between transgene and endogenous gene.

Targeted mutagenesis techniques, for example TILLING (Targeting Induced Local Lesions IN Genomes) and "deletea-gene" using fast-neutron bombardment, may be used to knockout gene function in a plant (Henikoff, et al., Plant Physiol. 135: 630-6 (2004); Li et al., Plant J. 27: 235-242 (2001)). TILLING involves treating seeds or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from plants in the mutagenized population. Amplified mutant genes may be annealed to wild-type genes to find mismatches between the mutant genes and wild-type genes. Detected differences may be traced back to the plants which had the mutant gene thereby revealing which mutagenized plants will have the desired expression (e.g. silencing of the gene of interest). These plants may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in plant genomes that can also be detected using PCR in a manner similar to TILLING.

Nucleic Acid Constructs

In accordance with one aspect of the invention, a sequence that suppresses a transcription factor that regulates alkaloid biosynthesis is incorporated into a nucleic acid construct that is suitable for introducing into a plant or cell. Thus, such a nucleic acid construct can be used to suppress at least one of NbTF1, NbTF3 NbTF4, NbTF5, NbTF6 and NbTF7. and optionally at least one of A622, NBB1, PMT, QPT, and MPO in a plant or cell.

In another aspect of the invention, a sequence that increases activity of transcription factor that regulates alkaloid biosynthesis is incorporated into a nucleic acid construct that is suitable for introducing into a plant or cell. Thus, such a nucleic acid construct can be used to overexpress NbTF1, NbTF3, NbTF4, NbTF5, NbTF6 and NbTF7, and optionally at least one of A622, NBB1, PMT, and QPT, and MPO in a plant or cell.

Recombinant nucleic acid constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence then is cloned into a vector containing suitable regulatory elements, such as upstream promoter and downstream terminator sequences.

An important aspect of the present invention is the use of nucleic acid constructs wherein an a sequence encoding a transcription factor that regulates alkaloid biosynthesis is operably linked to one or more regulatory sequences, which drive expression of the transcription factor-encoding sequence in certain cell types, organs, or tissues without unduly affecting normal development or physiology.

Promoters useful for expression of a nucleic acid sequence introduced into a cell to either decrease or increase expression of a transcription factor that regulates alkaloid biosynthesis may be constitutive promoters, such as the carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter). Tissue-specific, tissue-preferred, cell type-specific, and inducible promoters may be desirable under certain circumstances. For example, a tissue-specific promoter allows for overexpression in certain tissues without affecting expression in other tissues.

Preferred promoters include promoters which are active in root tissues, such as the tobacco RB7 promoter (Hsu et al., Pestic. Sci. 44: 9-19 (1995); U.S. Pat. No. 5,459,252), maize promoter CRWAQ81 (US published patent application 20050097633); the Arabidopsis ARSK1 promoter (Hwang and Goodman, Plant J. 8:37-43 (1995)), the maize MR7 promoter (U.S. Pat. No. 5,837,848), the maize ZRP2 promoter (U.S. Pat. No. 5,633,363), the maize MTL promoter (U.S. Pat. Nos. 5,466,785 and 6,018,099) the maize MRS1, MRS2, MRS3, and MRS4 promoters (U.S. Patent Publication No. 20050010974), an Arabidopsis cryptic promoter (U.S. Patent Publication No. 20030106105) and promoters that are activated under conditions that result in elevated expression of enzymes involved in nicotine biosynthesis such as the tobacco RD2 promoter (U.S. Pat. No. 5,837,876), PMT promoters (Shoji et al., Plant Cell Physiol. 41: 831-39 (2000); WO 2002/038588) or an A622 promoter (Shoji, et al., Plant Mol. Biol. 50: 427-40 (2002)).

The vectors of the invention may also contain termination sequences, which are positioned downstream of the nucleic acid molecules of the invention, such that transcription of mRNA is terminated, and polyA sequences added. Exemplary of such terminators include Agrobacterium tumefaciens nopaline synthase terminator (Tnos), Agrobacterium tumefaciens mannopine synthase terminator (Tmas) and the CaMV 35S terminator (T35S). Particularly preferred termination regions for use according to the invention include the pea ribulose bisphosphate carboxylase small subunit termination region (TrbcS) or the Tnos termination region. The expression vector also may contain enhancers, start codons, splicing signal sequences, and targeting sequences.

Expression vectors of the invention may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3'-O-phosphotransferase (kanamycin, neomycin and G418 resistance). These markers may include resistance to G418, hygromycin, bleomycin, kanamycin, and gentamicin. The construct may also contain the selectable marker gene bar that confers resistance to herbicidal phosphinothricin analogs like ammonium gluphosinate. Thompson et al, *EMBO J.* 9: 2519-23 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may be present in the vector, as is known in the art. For instance, when *Agrobacterium* is the host, T-DNA sequences may be included to facilitate the subsequent transfer to and incorporation into plant chromosomes.

Such gene constructs may suitably be screened for activity by transformation into a host plant via *Agrobacterium* and screening for modified alkaloid levels.

Suitably, the nucleotide sequences for the genes may be extracted from the Genbank™ nucleotide database and searched for restriction enzymes that do not cut. These restriction sites may be added to the genes by conventional methods such as incorporating these sites in PCR primers or by sub-cloning.

Preferably, constructs are comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al, Cloning Vectors. A Laboratory Manual, Elsevier, Amsterdam (1986). Particularly suitable vectors include the Ti plasmid vectors.

Host Plants and Cells

The present invention comprehends the genetic manipulation of a plant or cell via introducing a polynucleotide sequence that encodes a transcription factor that regulates alkaloid biosynthesis. Accordingly, the present invention provides methodology and constructs for reducing or increasing alkaloid synthesis in a plant. Additionally, the invention provides methods for producing alkaloids and related compounds in a plant cell.

A. Plants

The class of plants which can be used in the present invention is generally as broad as the class of alkaloid-producing higher plants amenable to genetic engineering techniques, including both monocotyledonous and dicotyledonous plants, as well as gymnosperms. A preferred alkaloid-producing plant includes a nicotinic alkaloid-producing plant of the *Nicotiana, Duboisia, Solanum, Anthocercis*, and *Salpiglessis* genera in the Solanaceae or the *Eclipta* and *Zinnia* genera in the Compositae.

As known in the art, there are a number of ways by which genes and gene constructs can be introduced into plants, and a combination of plant transformation and tissue culture techniques have been successfully integrated into effective strategies for creating transgenic crop plants.

These methods, which can be used in the present invention, have been described elsewhere (Potrykus, *Annu. Rev. Plant Physiol. Plant Mol. Biol.* 42: 205-225 (1991); Vasil, *Plant Mol. Biol.* 5: 925-937 (1994); Walden and Wingender, *Trends Biotechnol.* 13: 324-331 (1995); Songstad, et al., *Plant Cell, Tissue and Organ Culture* 40: 1-15 (1995)), and are well known to persons skilled in the art. For example, one skilled in the art will certainly be aware that, in addition to *Agrobacterium*-mediated transformation of *Arabidopsis* by vacuum infiltration (Bechtold et al., *C.R. Acad. Sci. Ser. III Sci. Vie*, 316: 1194-1199 (1993)) or wound inoculation (Katavic et al., *Mol. Gen. Genet.* 245: 363-370 (1994)), it is equally possible to transform other plant and crop species, using *Agrobacterium* Ti-plasmid-mediated transformation (e.g., hypocotyl (DeBlock et al., *Plant Physiol.* 91: 694-701 (1989)) or cotyledonary petiole (Moloney et al., *Plant Cell Rep.* 8: 238-242 (1989) wound infection), particle bombardment/biolistic methods (Sanford et al., *J. Part. Sci. Technol.* 5: 27-37 (1987); Nehra et al., *Plant J.* 5: 285-297 (1994); Becker et al., *Plant J.* 5: 299-307 (1994)) or polyethylene glycol-assisted protoplast transformation (Rhodes et al., *Science* 240: 204-207 (1988); Shimamoto et al., *Nature* 335: 274-276 (1989)) methods.

*Agrobacterium rhizogenes* may be used to produce transgenic hairy roots cultures of plants, including tobacco, as described, for example, by Guillon et al., *Curr. Opin. Plant Biol.* 9: 341-6 (2006). "Tobacco hairy roots" refers to tobacco roots that have T-DNA from an Ri plasmid of *Agrobacterium rhizogenes* integrated in the genome and grow in culture without supplementation of auxin and other phytohormones. Tobacco hairy roots produce nicotinic alkaloids as roots of a whole tobacco plant do.

Additionally, plants may be transformed by *Rhizobium, Sinorhizobium* or *Mesorhizobium* transformation. (Broothaerts et al., *Nature* 433: 629-633 (2005)).

After transformation of the plant cells or plant, those plant cells or plants into which the desired DNA has been incorporated may be selected by such methods as antibiotic resistance, herbicide resistance, tolerance to amino-acid analogues or using phenotypic markers.

Various assays may be used to determine whether the plant cell shows a change in gene expression, for example, Northern blotting or quantitative reverse transcriptase PCR (RT-PCR). Whole transgenic plants may be regenerated from the transformed cell by conventional methods. Such transgenic plants may be propagated and self pollinated to produce homozygous lines. Such plants produce seeds containing the genes for the introduced trait and can be grown to produce plants that will produce the selected phenotype.

Modified alkaloid content, effected in accordance with the present invention, can be combined with other traits of interest, such as disease resistance, pest resistance, high yield or other traits. For example, a stable genetically engineered transformant that contains a suitable transgene that modifies alkaloid content may be employed to introgress a modified alkaloid content trait into a desirable commercially acceptable genetic background, thereby obtaining a cultivar or variety that combines a modified alkaloid level with said desirable background. For example, a genetically engineered tobacco plant with reduced nicotine may be employed to introgress the reduced nicotine trait into a tobacco cultivar with disease resistance trait, such as resistance to TMV, blank shank, or blue mold. Alternatively, cells of a modified alkaloid content plant of the present invention may be transformed with nucleic acid constructs conferring other traits of interest.

B. Cells

The invention contemplates genetically engineering a cell with a nucleic acid sequence encoding a transcription factor that regulates alkaloid biosynthesis. Illustrative cells include but are not limited to cells of plants such *Nicotiana tabacum*, *Atropa belladonna*, *Hyoscyamus niger*, Additionally, cells expressing alkaloid biosynthesis genes may be supplied with precursors to increase substrate availability for alkaloid synthesis. Cells may be supplied with analogs of precursors which may be incorporated into analogs of naturally occurring alkaloids.

Constructs according to the invention may be introduced into any plant cell, using a suitable technique, such as *Agrobacterium*-mediated transformation, particle bombardment, electroporation, and polyethylene glycol fusion, or cationic lipid-mediated transfection.

Such cells may be genetically engineered with a nucleic acid construct of the present invention without the use of a selectable or visible marker and transgenic organisms may be identified by detecting the presence of the introduced construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, genetically engineered cells may be identified by recognizing differences in the growth rate or a morphological feature of a transformed cell compared to the growth rate or a morphological feature of a non-transformed cell that is cultured under similar conditions. See WO 2004/076625.

IV. Quantifying Alkaloid Content

A. Reduced Alkaloids

Pursuant to one aspect of the invention, genetically engineered plants and cells are characterized by reduced alkaloid content.

A quantitative reduction in alkaloid levels can be assayed by several methods, as for example by quantification based on gas-liquid chromatography, high performance liquid chromatography, radio-immunoassays, and enzyme-linked immunosorbent assays. In the present invention, alkaloid levels were measured by HPLC analysis performed on a Waters 2695 separations module equipped with a Waters X-Terra RP18 5 μm 4.6×150 mm with precolumn at a column temperature of 60°. The isocratic elution system consisted of 80% A:20% B where solvent A consisted of 50 mM citrate, 10 mM octanesulfonic acid pH 3.0 (adjusted with triethylamine) containing 5% methanol and solvent B was methanol over 15 min at a flow rate of 1 ml/min. Injection volume was 20 μl. Nicotine was detected at 261 nm via photodiode array detection.

In describing a plant of the invention, the phrase "decreased alkaloid plant" or "reduced alkaloid plant" encompasses a plant that has a decrease in alkaloid content to a level less than 50%, and preferably less than 10%, 5%, or 1% of the alkaloid content of a control plant of the same species or variety.

B. Increased Alkaloids

In one aspect of the invention, genetically engineered plants are characterized by increased alkaloid content. Similarly, genetically engineered cells are characterized by increased alkaloid production.

In describing a plant of the invention, the phrase "increased alkaloid plant" encompasses a genetically engineered plant that has an increase in alkaloid content greater than 10%, and preferably greater than 50%, 100%, or 200% of the alkaloid content of a control plant of the same species or variety.

A successfully genetically engineered cell is characterized by increased alkaloid synthesis. For example, an inventive genetically engineered cell may produce more nicotine compared to a control cell.

A quantitative increase in nicotinic alkaloid levels can be assayed by several methods, as for example by quantification based on gas-liquid chromatography, high performance liquid chromatography, radio-immunoassays, and enzyme-linked immunosorbent assays. In the present invention, alkaloid levels were measured by high performance liquid chromatography with a reversed phase column and a photodiode array detector as described above.

Products

The polynucleotide sequences that encode transcription factors that regulate alkaloid biosynthesis may be used for production of plants with altered alkaloid levels. Such plants may have useful properties, such as increased pest resistance in the case of increased-alkaloid plants, or reduced toxicity and increased palatability in the case of decreased-alkaloid plants.

Plants of the present invention may be useful in the production of products derived from harvested portions of the plants. For example, decreased-alkaloid tobacco plants may be useful in the production of reduced-nicotine cigarettes for smoking cessation. Increased-alkaloid tobacco plants may be useful in the production of modified risk tobacco products.

Additionally, plants and cells of the present invention may be useful in the production of alkaloids or alkaloid analogs including nicotine analogs, which may be used as therapeutics, insecticides, or synthetic intermediates. To this end, large-scale or commercial quantities of alkaloids and related compounds can be produced by a variety of methods, including extracting compounds from genetically engineered plant, cell, or culture system, including but not limited to hairy root cultures, suspension cultures, callus cultures, and shoot cultures.

In the following examples, functional genomics was used to elucidate six genes, NbTF1, NbTF2, NbTF4, NbTF5, NbTF6 and NbTF7, that encode transcription factors, that regulate alkaloid accumulation in *Nicotiana benthamiana*. Suppression of each of these six genes in *N. benthamiana* by virus-Induced gene silencing resulted in alteration of alkaloid levels. In four cases alkaloid levels were reduced, and in two cases alkaloid levels were increased. cDNA clones of NbTF1, NbTF2, NbTF4, NbTF5, NbTF6 and NbTF7 were obtained. Constructs for overexpression of the transcription factors were made and introduced into plant cells. The data from the present experiments indicate that the transcription factor nucleic acid sequences are useful in the production of plants and plants cells with altered alkaloid levels, in particular altered levels of nicotinic alkaloids.

These examples are meant to be illustrative only and are not to be read as limiting the present invention.

Example 1. Construction of Subtractive cDNA Libraries from *Nicotiana benthamiana* Roots, EST Sequencing and Selection of Transcription Factor Genes Nicotine biosynthesis occurs in the roots of *Nicotiana* species (Dawson, *Science* 94: 396-397 (1941)) and is induced by insect damage, wounding and the application of jasmonates (Winz and Baldwin, *Plant Physiol.* 125: 2189-2202 (2001)). In order to identify genes encoding transcription factors that control nicotine biosynthesis, we combined expressed sequence tag (EST) sequencing of methyljasmonate (MeJa)-induced roots of *Nicotiana benthamiana* with functional analysis using virus-induced gene silencing (VIGS) (Liu and Page, Plant Methods 4: 5 (2008)).

Hydroponic Cultivation of *Nicotiana benthamiana*

*Nicotiana benthamiana* Domin (Solanaceae) seedlings were grown hydroponically in 0.25× Hoagland's solution supplemented with iron chelate solution and oxygenated using an aquarium bubbler. Roots from three-week old plants were sampled before (t=0) and at 1, 4, and 7 hours after addition of MeJa to a final concentration of 11 µM. Total RNA was isolated from 450 mg each of untreated leaves, untreated roots, and a combined MeJa-treated root sample composed of 150 mg roots each from the 1, 4 and 7 hour time points using a RNeasy midi kit (Qiagen). We constructed three separate subtractive cDNA libraries: NBREL2, with mRNA pooled from MeJa-treated roots as tester and untreated root mRNA as driver; NBLEL3, with mRNA pooled from MeJa-treated roots as tester and leaf mRNA as driver; and NBREL4, with mRNA pooled from MeJa-treated roots as both tester and driver.

I.A.1.1 Construction of Subtracted VIGS-cDNA Libraries

A PCR-select subtractive cDNA library kit (Clontech) was used for cDNA synthesis with some modifications. Briefly, about 250 µg of total RNA was mixed with 300 µl of Oligo (dT)$_{25}$ Dynabeads (Dynal Biotech) in binding buffer (20 mM Tris-HCl pH 7.5, 1 M LiCl, 2 mM EDTA). After 10 min incubation, the beads were washed three times with washing buffer B (10 mM Tris-HCl pH 7.5, 0.15M LiCl, 1 mM EDTA), followed by washing twice with first strand buffer. The washed beads containing mRNA were resuspended in 40 µl of cDNA synthesis cocktail (8 µl 5× first strand buffer, 4 µl 10 mM dNTPs, 24 µl RNase-free water and 4 µl (8U) AMV reverse transcriptase) and incubated at 42° C. for 1.5 hours. The second strand synthesis was completed by addition of 120 µl of second strand synthesis cocktail (32 µl of 5× second strand buffer, 3.2 µl of 10 mM dNTPs, 8 µl of 20× enzyme cocktail and 77 µl RNase free water) and incubation at 16° C. for 2 hours, followed by addition of 4 µl (12U) T4 DNA polymerase and further incubation for 30 min. The reaction was stopped by addition of 20 µl 0.5 M EDTA. The beads were magnetically separated, the supernatant removed and the beads resuspended in 500 µl of wash buffer (5 mM Tris-HCl pH 7.5, 0.5 mM EDTA, 1 M NaCl, 1% SDS and 10 µg/ml glycogen) and heated at 75° C. for 15 min. The beads were then washed three times with wash buffer (5 mM Tris-HCl pH7.5, 0.5 mM EDTA, 1 M NaCl and 200 µg/ml BSA), followed by two more washes with RsaI buffer. The beads were resuspended in 84 µl H2O, 10 µl 10× RsaI buffer, 3 µl (30 U) RsaI, and incubated at 37° C. overnight. The free cDNA was isolated by magnetic separation of the beads and was used for adapter ligation, hybridizations and primary PCR as described in the manufacturer's protocol. Secondary PCR was performed using primers 5'-CG<u>GGATCC</u>TCGAGCGGCCGCCCGGGCAGGT-3' (BamH1 site underlined) (SEQ ID NO: 18) and 5'-CG<u>GAATTC</u>AGCGTGGTCGCGGCCGAGGT-3' (EcoR1 site underlined) (SEQ ID NO: 19). The PCR-select amplified cDNA fragments (700 ng) were digested with EcoRI and BamHI, followed by ligation into a similarly digested TRV-RNA2 vector, pYL156 (Liu et al., *Plant Journal* 30: 415-429 (2002)). The ligation mixture was electroporated into DH10B *E. coli* competent cells to give primary libraries. These was amplified on agar plates, plasmid DNA isolated and used to transform *Agrobacterium tumefaciens* C58 via electroporation. The ligation efficiency as determined by colony PCR was 98%.

I.A.1.2 EST Sequencing of Subtracted VIGS-cDNA Library and Identification of Transcription Factor Candidates To amplify cDNA inserts for sequencing, PCR was performed using vector primers 5'-GTTACTCAAGGAAGCACGATGAG-3' (SEQ ID NO: 20) and 5'-CAGTCGAGAATGTCAATCTCGTAG-3' (SEQ ID NO: 21) and randomly selected *A. tumefaciens* colonies as template. The resulting PCR products were sequenced directly using BigDye terminators and the primer 5'-GTTACTCAAGGAAGCACGATGAG-3' (SEQ ID NO: 20). 2016 ESTs were sequenced from NBREL2, and 1920 each from NBLEL3 and NBREL4. After removal of poor quality sequences, and combining of the three datasets, we obtained 3480 unique transcripts consisting of 606 contigs and 2874 singletons. The total VIGS-EST dataset was annotated via BLASTX comparison to the NCBI non-redundant database.

Using a combination of keyword searching on blastx annotations and blast analysis with transcription factors sequences, we identified 108 putative unique transcripts encoding transcription factors. These consisted of 24 contigs and 84 singletons.

Example 2. Screening of Transcription Factors for the Effect on Leaf Nicotine Accumulation Using VIGS We used virus-induced gene silencing (VIGS) (Baulcombe, *Curr. Opin. Plant Biol.* 2: 109-113 (1999); Lu et al., *Methods* 30: 296-303 (2003)) to test the effect of silencing the candidate transcription factor genes on nicotine biosynthesis.

I.A.1.3 VIGS silencing of Transcription Factors

VIGS constructs representing different transcription factors were tested for their ability to alter leaf nicotine levels both before and after application of MeJa to leaves. *N. benthamiana* plants were grown in soil in a controlled environment chamber with 16 hour/23° days and 8 hour/20° nights under approximately 100 µmol/m$^2$/s light intensity. Cultures of *A. tumefaciens* C58 containing the TRV-RNA1 plasmid or TRV-RNA2 constructs (pYL156) (both described in Liu et al., *Plant Journal* 30: 415-429 (2002) were grown overnight at 28° C. After centrifugation, the bacterial cell pellet was resuspended in infiltration buffer containing 1 mM MES (pH 5), 10 mM MgCl$_2$ and 100 µM acetosyringone to OD$_{600}$=1 and allowed to stand at room temperature for 3-6 hours before infiltration. Suspensions of TRV-RNA1 and pYL279 constructs were mixed 1:1 and infiltrated into the underside of the upper leaves of 3-4 week old plants using a 1 ml syringe. Negative control plants were infiltrated with buffer only or a TRV-RNA2 construct containing a non-functional fragment of green fluorescent protein (TRV-GFP). Plants were grown for 3 weeks before leaf nicotine levels in infected *N. benthamiana* plants were measured using ion-pair HPLC before and five days after application of MeJa (0.1% in a 0.1% Tween-20 solution sprayed on all leaf surfaces). A known gene encoding a nicotine biosynthetic enzyme (putrescine N-methyltransferase, PMT) was used as a positive control for VIGS knockdown of nicotine biosynthesis.

I.A.1.4 Nicotine Analysis by Ion Pair HPLC

Young (~3-5 cm) *N. benthamiana* leaves were sampled by excising one half of a leaf from each plant. After determining fresh weight of the sample, 200 μl of zirconium beads and 300 μl of 50 mM citrate buffer pH 3:methanol (70:30) were added, the sample as homogenized with a Beadbeater followed by incubation in an ultrasonic bath for 10 min. The resulting extract was incubated at 4° overnight before centrifugation and filtration (0.45 μm, Spin-X) to clarify the extract. Ion-pair HPLC analysis was performed on a Waters 2695 separations module equipped with a Waters X-Terra RP18 5 μm 4.6×150 mm with precolumn at a column temperature of 60°. The isocratic elution system consisted of 80% A:20% B where solvent A consisted of 50 mM citrate, 10 mM octanesulfonic acid pH 3.0 (adjusted with triethylamine) containing 5% methanol and solvent B was methanol over 15 min at a flow rate of 1 ml/min. Injection volume was 20 μl. Nicotine was detected at 261 nm via photodiode array detection. Quantification was performed using peak area by comparison to a standard curve ($r^2$ 0.999) derived from injection of solutions of authentic nicotine ranging in concentration from 1040 μg/ml to 10.4 μg/ml.

Of the 108 transcription factors tested, VIGS of four led to reduced nicotine levels (NbTF1, NbTF4, NbTF5, NbTF6) and VIGS of two gave increased constitutive nicotine levels (NbTF7) or increased levels after MeJa application (NbTF3) (FIG. 1). Buffer and TRV-GFP control plants had similar nicotine levels, indicating that TRV infection had little influence on nicotine biosynthesis. As expected, the silencing of putrescine N-methyltransferase, a key enzyme in the nicotine pathway, led to substantial reductions in leaf nicotine.

Example 2. Cloning of Full-Length cDNAs for Transcription Factors Affecting Leaf Nicotine Accumulation I.A.1.5 Full-Length cDNAs were Obtained Using Rapid Amplification of cDNA Ends (RACE) PCR.

I.A.1.6 NbTF1

I.A.1.7 5' and 3' RACE PCR was used to obtain the full-length cDNA sequence of NbTF1. The full-length NbTF1 transcript was 2313 bp in length encoding an open reading frame (ORF) of 2040 bp. The sequence of the NbTF1 gene from *N. benthamiana* is set forth in SEQ ID NO: 1. The sequence of the NbTF1 open reading frame (ORF) is set forth in SEQ ID NO: 2. The predicted amino acid sequence of *N. benthamiana* NbTF1 is set forth in SEQ ID NO: 3.

I.A.1.8 NbTF3

I.A.1.9 The NbTF3 sequence identified from the EST sequencing was a 295 bp singleton that was extended via genome walking (Genome Walker kit, Clontech), to yield a 626 bp fragment. Despite the use of 5' and 3' RACE PCR and further application of genome walking, we did not obtain additional sequence information for NbTF3. The partial sequence of the NbTF3 gene from *N. benthamiana* is set forth in SEQ ID NO: 4

I.A.1.10 NbTF4

I.A.1.11 Genome walking was used to obtain the full-length cDNA sequence of NbTF4. The open reading frame (ORF) of NbTF4 is 759 bp. The sequence of the NbTF4 gene is set forth in SEQ ID NO: 5. The NBTF4 ORF is set forth in SEQ ID NO: 6. The predicted amino acid sequence of the *N. benthamiana* NbTF4 is set forth in SEQ ID NO: 7.

I.A.1.12 NbTF5

I.A.1.13 Blast searching of a conventional *N. benthamiana* root cDNA library was used to obtain the full-length cDNA clone of NbTF5. The full-length NbTF5 gene was 2401 bp in length encoding an open reading frame (ORF) of 1971 bp. The sequence of the NbTF5 gene from *N. benthamiana* is set forth in SEQ ID NO: 8. The NbTF5 ORF sequence is set forth in SEQ ID NO: 9. The predicted amino acid sequence of the *N. benthamiana* NbTF5 is set forth in SEQ ID NO: 10.

I.A.1.14 NbTF6

I.A.1.15 5' and 3' RACE PCR was used to obtain the full-length sequence of NbTF6. The full-length NbTF6 gene was 958 bp in length encoding an open reading frame (ORF) of 669 bp. The sequence of the NbTF6 gene from *N. benthamiana* is set forth in SEQ ID NO: 11. The NbTF6 ORF is set forth in SEQ ID NO: 12. The predicted amino acid sequence of the *N. benthamiana* NbTF6 is set forth in SEQ ID NO: 13.

I.A.1.16 NbTF7

I.A.1.17 5' and 3' RACE PCR and GenomeWalking were used to obtain the full-length sequence of NbTF7. The full-length NbTF7 gene was 3299 bp in length encoding an open reading frame (ORF) of 2667 bp. The sequence of the NbTF7 gene from *N. benthamiana* is set forth in SEQ ID NO: 14. The NbTF7 ORF sequence is set forth in SEQ ID NO: 15. The predicted amino acid sequence of the *N. benthamiana* NbTF7 is set forth in SEQ ID NO: 16

The six transcription factors represented several different classes of transcription factors. These classifications, and the DNA sequence of the associated cis-element to which they bind, are shown in Table 1.

TABLE 1

Classification of *N. benthamiana* transcription factors

| Name | Transcription Factor Class | Associated cis-element |
| --- | --- | --- |
| NbTF1 | Myc, basic helix-loop-helix (bHLH) | G-box CACGTG |
| NbTF3 | Myc, basic helix-loop-helix (bHLH) | G-box CACGTG |
| NbTF4 | Homeodomain leucine zipper | |
| NbTF5 | Myc, basic helix-loop-helix (bHLH) | G-box CACGTG |
| NbTF6 | AP2, ethylene-response factor | GCC-box AGCCGCC |
| NbTF7 | B3 domain, auxin response factor | CACCTG |

Example 3. Modifying Alkaloid Biosynthesis in Transgenic Plants

We used stable transformation of *N. benthamiana* to introduce the six transcription factor genes as both sense overexpression constructs (for NbTF1, NbTF4, NbTF5, NbTF6, NbTF7) and RNA interference (RNAi) constructs (for all six transcription factors). Open reading frames (for overexpression) and cDNA fragments (for RNAi) were amplified using PCR and cloned into the Gateway® entry vector pCR8/GW/TOPO (Invitrogen) or pENTR-D/TOPO (Invitrogen). Overexpression constructs were recombined into the Gateway® plant transformation vector pK7WG2 using LR clonase (Invitrogen). Similarly, RNAi constructs were recombined into the Gateway® RNAi vector pK7GW1WG2(I). All cloning procedures were performed in *E. coli* and final, sequence confirmed constructs were transformed into *Agrobacterium tumefaciens* C58. Plants were transformed using leaf disc methods adapted from Draper et al. (In: Plant Genetic Transformation and Gene Expression: A Laboratory Manual, pp. 97-144. Draper, J., Scott, R., et al.

(eds.), Blackwell Scientific Publications (1988)). Briefly leaf discs excised from mature *N. benthamiana* plants were surface sterilized, incubated in *Agrobacterium* culture containing the construct of interest and then placed on MS agar plates for two to four days. The leaf disks are transferred to shoot regeneration agar media plus 300 μg/ml timentin and 100 μg/ml kanamycin. After four and six weeks shoots that had formed on callus tissue were excised and transferred to MS+timentin+kanamycin agar plates. After roots had developed, plantlets were transferred to soil to form T0 plants.

Genomic DNA was isolated from each T0 plant and the presence or absence of transgenes was determined using PCR. Primers were designed to anneal to transformation vector and the transcription factor construct. T0 plants shown to be transgenic by PCR were analyzed using ion-pair HPLC to determine leaf nicotine levels. Nicotine was measured in samples containing three leaf discs (~50 mg FW) and converted to a fresh weight basis. Wild-types varied between batches of regenerated plants due to differences in growing conditions.

Figure 2:
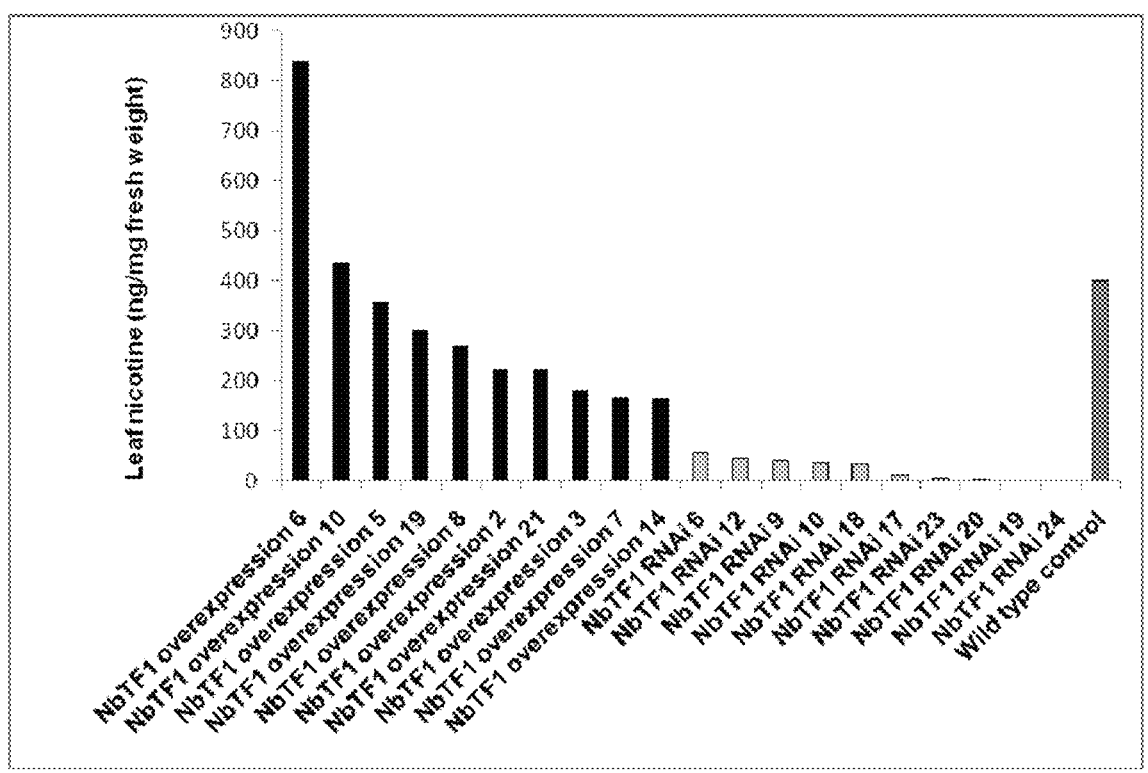
FIG. 2 depicts leaf nicotine levels in *N. benthamiana* plants transformed with constructs for overexpression or suppression of NbTF1.

Silencing NbTF1 via RNAi constructs led to reduction of leaf nicotine in several of the transgenic lines as compared to both sense overexpression and wild-type control plants (FIG. 2). Sense overexpression of NbTF1 lead to an increase in leaf nicotine levels in line NbTF1 overexpression 6.

Figure 3:
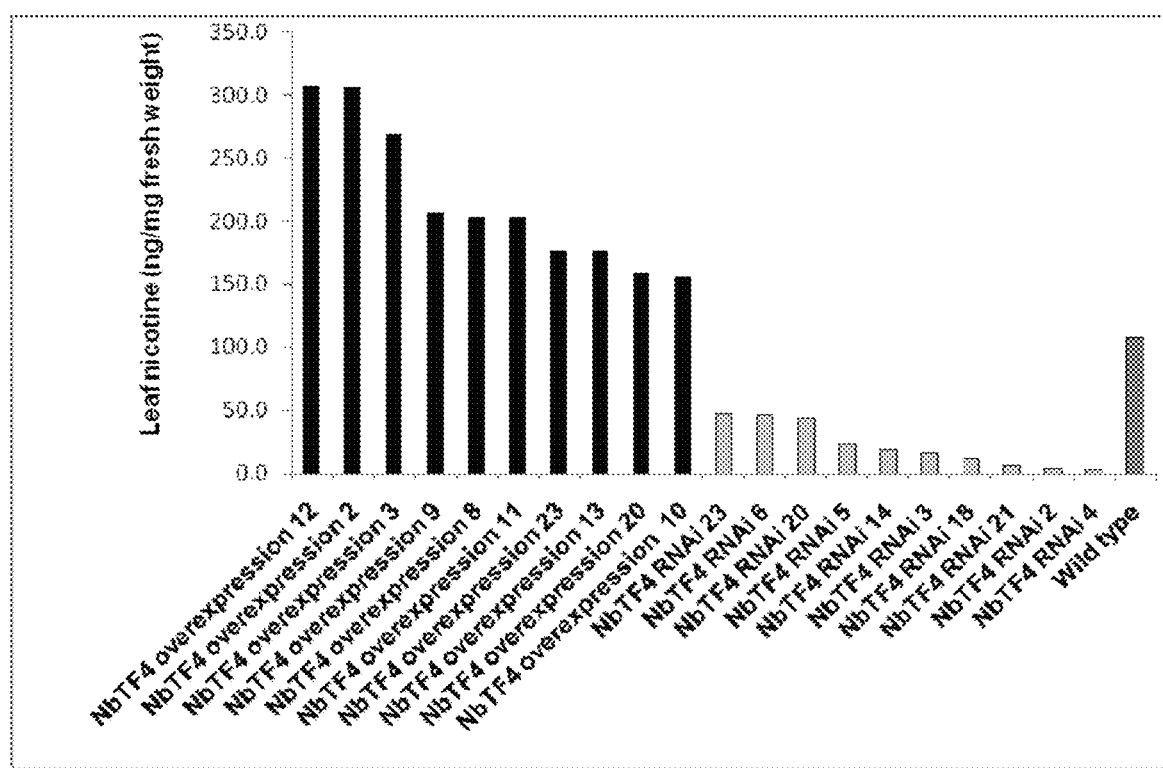
FIG. 3 depicts leaf nicotine levels in *N. benthamiana* plants transformed with constructs for overexpression or suppression of NbTF4.

Overexpression of NbTF4 led to an increase in leaf nicotine compared to wild-type plants, while NbTF4 silencing via RNAi gave reduced levels (FIG. 3).

Figure 4:
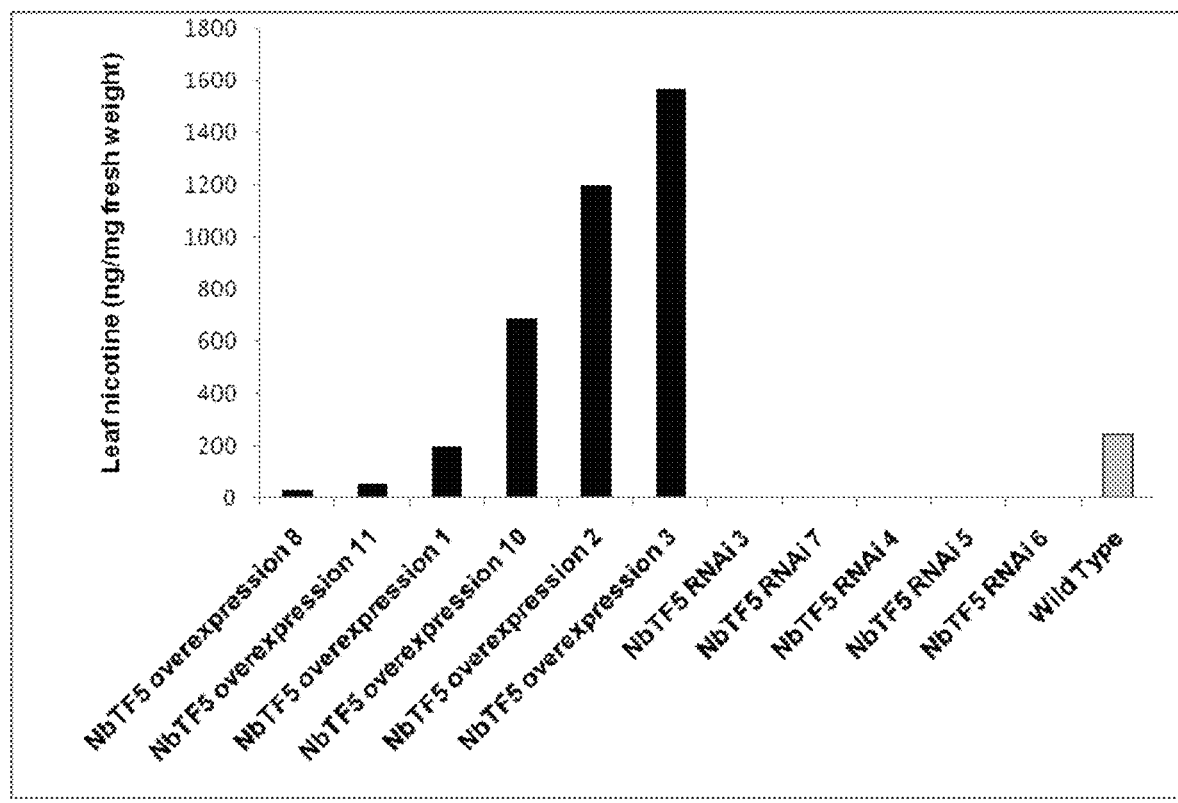
FIG. 4 depicts leaf nicotine levels in *N. benthamiana* plants transformed with constructs for overexpression or suppression of NbTF5.

Overexpression of NbTF5 led to large increases in leaf nicotine levels while RNAi silencing of this gene resulted in an almost complete block in nicotine accumulation (FIG. 4).

Transformation of plants with inverted repeats of segments of NbTF3, NbTF6 or NbTF7 in the plasmid pK7GW1WG2(I) did not result in lines with phenotypes similar to those seen in plants with VIGS of the same gene. This may indicate VIGS was more effective in silencing expression in the cells in which nicotine synthesis occurs.

What is claimed is:

1. A method of producing a reduced nicotinic alkaloid-producing plant, wherein the method comprises:
   (a) providing a population of mutated *Nicotiana* plants;
   (b) detecting and selecting a target mutated *Nicotiana* plant within the population, wherein the target mutated *Nicotiana* plant has decreased expression of a NbTF5 transcription factor, wherein the amino acid sequence of the NbTF5 transcription factor is set forth in SEQ ID NO: 10, and wherein the transcription factor is encoded by a nucleotide sequence selected from the group consisting of:
      (i) a nucleotide sequence set forth in SEQ ID NO: 8 or SEQ ID NO: 9; and
      (ii) a nucleotide sequence that encodes a polypeptide having the amino acid sequence set forth in SEQ ID NO: 10; and
   (c) selectively breeding the target mutated *Nicotiana* plant to produce a population of *Nicotiana* plants having decreased expression of the NbTF5 transcription factor.

2. The method of claim 1, wherein the detecting comprises:
   (a) using primers developed from SEQ ID NO: 8 or SEQ ID NO: 9 to amplify regions of the NbTF5 transcription factor gene from mutated *Nicotiana* plants in the population of mutated *Nicotiana* plants;
   (b) identifying mismatches between the amplified regions and corresponding regions in a wild-type gene that lead to decreased expression of the NbTF5 transcription factor; and
   (c) identifying the mutated *Nicotiana* plant that comprises the mismatches.

3. A mutated *Nicotiana* plant,
   wherein the mutated *Nicotiana* plant comprises a mutation in a gene encoding a NbTF5 transcription factor, wherein the amino acid sequence of the NbTF5 transcription factor is set forth in SEQ ID NO: 10, wherein the transcription factor is encoded by a nucleotide sequence selected from the group consisting of:
   (a) a nucleotide sequence set forth in SEQ ID NO: 8 or SEQ ID NO: 9; and
   (b) a nucleotide sequence that encodes a polypeptide having the amino acid sequence set forth in SEQ ID NO: 10; and
      wherein the mutated *Nicotiana* plant further comprises a reduced expression of the NbTF5 transcription factor and reduced nicotinic alkaloid content as compared to a control *Nicotiana* plant.

4. A method of producing the mutated *Nicotiana* plant of claim 3, comprising down-regulating a NbTF5 transcription factor wherein the NbTF5 transcription factor is down-regulated by:

(a) genetically engineering a population of *Nicotiana* plant cells to eliminate production of a protein encoded by the NbTF5 gene comprising the nucleotide sequence set forth in SEQ ID NO: 8, comprising introducing one or more mutations into the region of SEQ ID NO: 8 that encodes a polypeptide having the amino acid sequence set forth in SEQ ID NO: 10; and (b) detecting and selecting a target mutated *Nicotiana* plant cell or a *Nicotiana* plant derived from such a cell, wherein the target mutated *Nicotiana* plant cell or *Nicotiana* plant has a mutation in the NbTF5 gene and wherein the targeted *Nicotiana* plant cell or *Nicotiana* plant has a decreased nicotinic alkaloid content as compared to a control *Nicotiana* plant cell or *Nicotiana* plant.

5. The method of claim 4, wherein the genetic engineering further comprises introducing into the population of *Nicotiana* plant cells a reagent comprising a recombinagenic oligonucleobase.

6. The method of claim 4, wherein the genetic engineering further comprises introducing into the population of *Nicotiana* plant cells a reagent comprising a targeted nuclease.

7. The mutated *Nicotiana* plant of claim 3, wherein the plant is a *Nicotiana tabacum* plant.

8. A product having a reduced level of a nicotinic alkaloid comprising the mutated *Nicotiana* plant of claim 3, or portions thereof, as compared to a product produced from a control *Nicotiana* plant.

9. The product of claim 8, wherein the product is selected from the group consisting of a cigarette, cigarette tobacco, cigar tobacco, a cigar, pipe tobacco, chewing tobacco, snuff, snus, lozenges, and reconstituted tobacco.

10. Seeds from the mutated *Nicotiana* plant of claim 3.

11. The method of claim 4, wherein the genetic engineering further comprises suppressing within the *Nicotiana* plant at least one of NBB1, A622, quinolate phospho-ribosyltransferase (QPT), putrescine-N-methyltransferase (PMT) and N-methylputrescine oxidase (MPO).

12. The method of claim 4, wherein the genetic engineering further comprises suppressing within the *Nicotiana* plant at least one transcription factor that positively regulates nicotinic alkaloid biosynthesis selected from NbTF1, NbTF4, and NbTF6.

13. The method of claim 4, wherein the genetic engineering further comprises overexpressing within the *Nicotiana* plant at least one transcription factor that negatively regulates nicotinic alkaloid biosynthesis selected from NbTF3 and NbTF7.

* * * * *

UNITED STATES PATENT AND TRADEMARK OFFICE
CERTIFICATE OF CORRECTION

PATENT NO. : 10,941,410 B2
APPLICATION NO. : 15/996064
DATED : March 9, 2021
INVENTOR(S) : Page et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 146 days.

Signed and Sealed this
Thirty-first Day of January, 2023

Katherine Kelly Vidal
*Director of the United States Patent and Trademark Office*

SEQUENCE LISTING

```
<160> NUMBER OF SEQ ID NOS: 21

<210> SEQ ID NO 1
<211> LENGTH: 2313
<212> TYPE: DNA
<213> ORGANISM: Nicotiana benthamiana

<400> SEQUENCE: 1
aagcaaactc aaacccattt gcctattatt ctctctcatg tctttctatc atcccctacg      60
ttctctctct ctatatatat ctttcacgcc accatttcaa acttttgtg  ctgggtttat     120 ggaatgactg attacagatt acccaccatg aatttgtgga atgctagtgg tagtaccgat     180
gacaacgttt ctatgatgga agctttgata tcttctgatc tcacctcatt ttgtgctact     240
tctaattctt ctgctgctgc tattactgct aattctaatc atattccagt taatacccga     300
acggttcttc ttccgtcttc ttgtgcttct actgtcacag ctgtgcctgt cgatgcttca     360
aaatcgatgt cttatttcaa ccaagaaact cttcaacagc gtctccaaac cctcattgat     420
ggtgctcgtg aaacgtggac ctacgccata ttttggcagt catccgttgt tgatttaacg     480
agtccgattt tgttggtctg gggagatggt tactacaaag gtgaagaaga taaagccaat     540
aggaaattag ctgtttcttc tcctgcttat atagctgagc aagaacaccg gaaaaaggtt     600
ctccgtgagc tgaattcgtt gatctccggc acgcaaaccg gcactaatga tgccgtcgat     660
gaagaagtta ccgacactga atggttcttc cttatttcca tgaccccatc gtttgttaac     720
ggaagtgggc ttccgggtca ggccttatac aattccagcc ctatttgggt cttcggagca     780
gagaaattgg cagcttccca ctgcgaacgg gctcggcagg cccagggatt cgggcttcag     840
acaatggttt gtattccttc agcaaacggc gtggttgaat tgggctccac ggagttgatt     900
attcagagtt ctgatatcat caacaaggtt agagtattgt ttaacttcaa taatgatttg     960
ggctctggtt cgtgggctgt gcagcccgag agcgatccgt ccgctctttg gctcactgat    1020
ccatcgcctg cagctgtacc tgtgaaagat ttaaatacag ttgaggcaaa ttcagttcca    1080
ccaagtaata gtagtaagca acttgtgttt gataatgaga ataatggtca aagttgtgat    1140
aatcagcaac agcaccattc tcagcaacaa acacaaggat ttttcacaag ggagttgaat    1200
ttttcagaat tcgggtttga tggatgtaat aatattagga atggtaattc atcagtttct    1260
tgcaagccag agtcggggga aatcttgaat ttttgtgata gccctaagaa aagtgcaaat    1320
```

```
gggaacttat tttcgtgtca gtcccatttt ggggcagggg aggagaataa gaacaagaaa    1380
aggtcagctg cttccagagg aagcaatgaa gaaggaatgc tttcatttgt ttcaggtaca    1440
atcttgcctg cagcttctgg tgcgatgaag tcaattggat gcgtcgctga aggctcctct    1500
gatcattcag atcttgaggc ctcactggtg aaagaagctg aaagtagtag agttgtagaa    1560
cccgaaaaga ggccaaagaa gcgaggaagg aagccagcaa atggacgtga ggaacctttg    1620
aatcacgtcg aagcagagag gcaaggagag agaaattaa ccaaaggtt ctacgcttta     1680 agagctgttg ttccgaatgt gtccaaaatg gacaaggcat cactgcttgg agatgcaatt    1740
tcatatatta atgagctgaa gttgaagctt caaaatacag aaacagatag ggaaaacttg    1800
aagagccaaa tagaagattt gaagaaagaa ttagctagta aagactcaag gcgccctggt    1860
cctccaccac caaatcaaga tcacaagatg tctagccata ctgggagcaa ggttgtagat    1920
gtggatatag atgttaaggt aattggatgg gatgcgatga ttagtgtaca atgtaataaa    1980
aataaccacc cagctgcaag gttaatggta gccctcaagg agttagatct agatgtgcac    2040
catgccagtg tttcagtggt gaacgatttg atgatccaac aagccacagt gaaaatgggt    2100
agcagacttt acacggaaga gcaacttagg atagcattga catccagagt tgctgaaaca    2160
cgctaaaaac acttcacatc tcaatttgta ggctttgagt tagccttgta aattgtgttc    2220
gagtctatgc taaatttaag gctctgctta agagctctat ctaatgtttt tgtcatcaat    2280
ttagagatta agatgaaggc tcttgttgtg tta                                2313

<210> SEQ ID NO 2
<211> LENGTH: 2040
<212> TYPE: DNA
<213> ORGANISM: Nicotiana benthamiana

<400> SEQUENCE: 2
atgactgatt acagattacc caccatgaat ttgtggaatg ctagtggtag taccgatgac      60
aacgtttcta tgatggaagc tttgatatct tctgatctca cctcattttg tgctacttct     120
aattcttctg ctgctgctat tactgctaat tctaatcata ttccagttaa taccgaacg      180 gttcttcttc cgtcttcttg tgcttctact gtcacagctg tgcctgtcga tgcttcaaaa    240
tcgatgtctt atttcaacca agaaactctt caacagcgtc tccaaaccct cattgatggt    300
gctcgtgaaa cgtggaccta cgccatattt tggcagtcat ccgttgttga tttaacgagt    360
ccgattttgt tggtctgggg agatggttac tacaaaggtg aagaagataa agccaatagg    420
aaattagctg tttcttctcc tgcttatata gctgagcaag aacaccggaa aaaggttctc    480
cgtgagctga attcgttgat ctccggcacg caaaccggca ctaatgatgc cgtcgatgaa    540
gaagttaccg acactgaatg gttcttcctt atttccatga ccccatcgtt tgttaacgga    600
agtgggcttc cgggtcaggc cttatacaat tccagcccta tttgggtctt cggagcagag    660
aaattggcag cttcccactg cgaacgggct cggcaggccc agggattcgg gcttcagaca    720
atggtttgta ttccttcagc aaacggcgtg gttgaattgg gctccacgga gttgattatt    780
cagagttctg atatcatcaa caaggttaga gtattgttta acttcaataa tgatttgggc    840
tctggttcgt gggctgtgca gcccgagagc gatccgtccg ctctttggct cactgatcca    900
tcgcctgcag ctgtacctgt gaaagattta aatacagttg aggcaaattc agttccacca    960
agtaatagta gtaagcaact tgtgtttgat aatgagaata atggtcaaag ttgtgataat    1020
cagcaacagc accattctca gcaacaaaca caaggatttt tcacaaggga ttgaattttt    1080
tcagaattcg ggtttgatgg atgtaataat attaggaatg gtaattcatc agtttcttgc    1140
```

-continued

```
aagccagagt cggggaaat cttgaatttt tgtgatagcc ctaagaaaag tgcaaatggg    1200
aacttatttt cgtgtcagtc ccattttggg gcaggggagg agaataagaa caagaaaagg    1260
tcagctgctt ccagaggaag caatgaagaa ggaatgcttt catttgtttc aggtacaatc    1320
ttgcctgcag cttctggtgc gatgaagtca attggatgcg tcgctgaagg ctcctctgat    1380
cattcagatc ttgaggcctc actggtgaaa gaagctgaaa gtagtagagt tgtagaaccc    1440
gaaaagaggc caaagaagcg aggaaggaag ccagcaaatg gacgtgagga acctttgaat    1500
cacgtcgaag cagagaggca aaggagagag aaattaaacc aaaggttcta cgctttaaga    1560
gctgttgttc cgaatgtgtc caaaatggac aaggcatcac tgcttggaga tgcaatttca    1620
tatattaatg agctgaagtt gaagcttcaa aatacagaaa cagataggga aaacttgaag    1680
agccaaatag aagatttgaa gaaagaatta gctagtaaag actcaaggcg ccctggtcct    1740
ccaccaccaa atcaagatca caagatgtct agccatactg ggagcaaggt tgtagatgtg    1800
gatatagatg ttaaggtaat tggatgggat gcgatgatta gtgtacaatg taataaaaat    1860
aaccacccag ctgcaaggtt aatggtagcc ctcaaggagt tagatctaga tgtgcaccat    1920
gccagtgttt cagtggtgaa cgatttgatg atccaacaag ccacagtgaa atgggtagc    1980 agactttaca cggaagagca acttaggata gcattgacat ccagagttgc tgaaacacgc    2040
```

<210> SEQ ID NO 3
<211> LENGTH: 680
<212> TYPE: PRT
<213> ORGANISM: Nicotiana benthamiana

<400> SEQUENCE: 3

```
Met Thr Asp Tyr Arg Leu Pro Thr Met Asn Leu Trp Asn Ala Ser Gly
1               5                   10                  15

Ser Thr Asp Asp Asn Val Ser Met Met Glu Ala Leu Ile Ser Ser Asp
            20                  25                  30

Leu Thr Ser Phe Cys Ala Thr Ser Asn Ser Ser Ala Ala Ala Ile Thr
        35                  40                  45

Ala Asn Ser Asn His Ile Pro Val Asn Thr Arg Thr Val Leu Leu Pro
    50                  55                  60

Ser Ser Cys Ala Ser Thr Val Thr Ala Val Pro Val Asp Ala Ser Lys
65                  70                  75                  80

Ser Met Ser Tyr Phe Asn Gln Glu Thr Leu Gln Gln Arg Leu Gln Thr
                85                  90                  95

Leu Ile Asp Gly Ala Arg Glu Thr Trp Thr Tyr Ala Ile Phe Trp Gln
            100                 105                 110

Ser Ser Val Val Asp Leu Thr Ser Pro Ile Leu Leu Val Trp Gly Asp
        115                 120                 125

Gly Tyr Tyr Lys Gly Glu Glu Asp Lys Ala Asn Arg Lys Leu Ala Val
    130                 135                 140

Ser Ser Pro Ala Tyr Ile Ala Glu Gln Glu His Arg Lys Lys Val Leu
145                 150                 155                 160

Arg Glu Leu Asn Ser Leu Ile Ser Gly Thr Gln Thr Gly Thr Asn Asp
                165                 170                 175

Ala Val Asp Glu Glu Val Thr Asp Thr Glu Trp Phe Phe Leu Ile Ser
            180                 185                 190

Met Thr Pro Ser Phe Val Asn Gly Ser Gly Leu Pro Gly Gln Ala Leu
        195                 200                 205

Tyr Asn Ser Ser Pro Ile Trp Val Phe Gly Ala Glu Lys Leu Ala Ala
    210                 215                 220
```

```
Ser His Cys Glu Arg Ala Arg Gln Ala Gln Gly Phe Gly Leu Gln Thr
225                 230                 235                 240

Met Val Cys Ile Pro Ser Ala Asn Gly Val Val Glu Leu Gly Ser Thr
            245                 250                 255

Glu Leu Ile Ile Gln Ser Ser Asp Ile Ile Asn Lys Val Arg Val Leu
        260                 265                 270

Phe Asn Phe Asn Asn Asp Leu Gly Ser Gly Ser Trp Ala Val Gln Pro
    275                 280                 285

Glu Ser Asp Pro Ser Ala Leu Trp Leu Thr Asp Pro Ser Pro Ala Ala
290                 295                 300

Val Pro Val Lys Asp Leu Asn Thr Val Glu Ala Asn Ser Val Pro Pro
305                 310                 315                 320

Ser Asn Ser Ser Lys Gln Leu Val Phe Asp Asn Glu Asn Asn Gly Gln
                325                 330                 335

Ser Cys Asp Asn Gln Gln Gln His His Ser Gln Gln Gln Thr Gln Gly
                340                 345                 350

Phe Phe Thr Arg Glu Leu Asn Phe Ser Glu Phe Gly Phe Asp Gly Cys
            355                 360                 365

Asn Asn Ile Arg Asn Gly Asn Ser Ser Val Ser Cys Lys Pro Glu Ser
    370                 375                 380

Gly Glu Ile Leu Asn Phe Cys Asp Ser Pro Lys Lys Ser Ala Asn Gly
385                 390                 395                 400

Asn Leu Phe Ser Cys Gln Ser His Phe Gly Ala Gly Glu Glu Asn Lys
                405                 410                 415

Asn Lys Lys Arg Ser Ala Ala Ser Arg Gly Ser Asn Glu Glu Gly Met
            420                 425                 430

Leu Ser Phe Val Ser Gly Thr Ile Leu Pro Ala Ala Ser Gly Ala Met
            435                 440                 445

Lys Ser Ile Gly Cys Val Ala Glu Gly Ser Ser Asp His Ser Asp Leu
    450                 455                 460

Glu Ala Ser Leu Val Lys Glu Ala Glu Ser Ser Arg Val Val Glu Pro
465                 470                 475                 480

Glu Lys Arg Pro Lys Lys Arg Gly Arg Lys Pro Ala Asn Gly Arg Glu
                485                 490                 495

Glu Pro Leu Asn His Val Glu Ala Glu Arg Gln Arg Arg Glu Lys Leu
            500                 505                 510

Asn Gln Arg Phe Tyr Ala Leu Arg Ala Val Val Pro Asn Val Ser Lys
        515                 520                 525

Met Asp Lys Ala Ser Leu Leu Gly Asp Ala Ile Ser Tyr Ile Asn Glu
530                 535                 540

Leu Lys Leu Lys Leu Gln Asn Thr Glu Thr Asp Arg Glu Asn Leu Lys
545                 550                 555                 560

Ser Gln Ile Glu Asp Leu Lys Lys Glu Leu Ala Ser Lys Asp Ser Arg
                565                 570                 575

Arg Pro Gly Pro Pro Pro Asn Gln Asp His Lys Met Ser Ser His
            580                 585                 590

Thr Gly Ser Lys Val Val Asp Val Asp Ile Asp Val Lys Val Ile Gly
            595                 600                 605

Trp Asp Ala Met Ile Ser Val Gln Cys Asn Lys Asn Asn His Pro Ala
    610                 615                 620

Ala Arg Leu Met Val Ala Leu Lys Glu Leu Asp Leu Asp Val His His
625                 630                 635                 640
```

```
Ala Ser Val Ser Val Val Asn Asp Leu Met Ile Gln Gln Ala Thr Val
            645                 650                 655

Lys Met Gly Ser Arg Leu Tyr Thr Glu Glu Gln Leu Arg Ile Ala Leu
        660                 665                 670

Thr Ser Arg Val Ala Glu Thr Arg
        675                 680

<210> SEQ ID NO 4
<211> LENGTH: 626
<212> TYPE: DNA
<213> ORGANISM: Nicotiana benthamiana

<400> SEQUENCE: 4
gcactattca ctagtaacct agaccaggta ctacatatct agcctcttta ttcattcaca      60
tttatcttca tctttcttca acccttacc tttataattt ccctcaccaa aaatacacaa     120
tcatatcttt aaaaaatat tatcaagaaa aaatggatga actaatggtc tcctcttctt     180
cctcttcctc atcattttcc ataccctctt tgttttctca aacaaaccaa cctttatcta     240
cccttcaaca aatgcttcaa catattctca aaaatcaagt agattgttgg tcttatgcta     300
ttttttggca aacttcaaat gatgatgatg gccgtttatt tttagcatgg ggtgatggtc     360
atttccatgg tactaaaatg aaaaaaggtg aagtaaatgg tgctaataaa gctagttctt     420
tagagagaaa aaatgttata aaggaatga atacaagctt tgatttgtga aaatggagat     480
ggtgtagtag atgggggtga tgttactgat attgaatggt tttatgttat gtctttagct     540
caaatctttt tctattggtg atggaattcc tggtaaagct tttagtactg attcttttgt     600
gtggttaaat ggggcacaac aacttc                                          626

<210> SEQ ID NO 5
<211> LENGTH: 1844
<212> TYPE: DNA
<213> ORGANISM: Nicotiana benthamiana

<400> SEQUENCE: 5
cgacggcccg ggctggtatc tccttctcaa ccagacatat aagagttctg acatcctaac      60
atatcaaggt agaagatgtt agcaattta acaaaaatat tttctttcat atatcataaa     120
aggcgatgaa acaaagacat gtaaagtaa atataatgca agaataaga aggtatcaat     180 caatgaaaat agattcttga taattacaca gagtaaaaac gtgaatcacg tagccgacac     240
ccatctgata atataattag gagggaactg ttgaatgaag caacgatga ttatatataa     300 agatgacaag taaacaccac taaagtttaa ctccactaaa gtttgataaa ccatagaata     360
tagtattagg ataatctgag atggctcgat gtggacttgg agctagaagc cagccaacta     420
actacaagcc ccaattagta cgcccctgg ttattgggga aaaagaaaa ccaatcacca      480 aatcaaccaa aaaaagata ctacagtgga aaacaagag gggttaaagg aataaacaat      540
aaacaacgat cataaactta caaaaggaa gtaatatacg atataactag gacccacccc     600
ttcttcagtc catataaaaa ttattgggca aagttgaaaa attcccctac cagaactctt     660
aacaccataa atatactatt ctatcaactg tgtcagaggt acatgaacat tccaattcca     720
atccacatcc acatatatat aagtcccaac tccagcaatc tcagaaacac ttttggtgt     780 tagctttggc atatgattgg atcttgagaa gatgtttgat gtaggggaat ttcttgtac     840 ttcttcagca gctgctctta ttctgcaga gtgtttcagt agtggcagct tcagcagttt     900
accatcctca aagaagaaga aggttaataa caagaatacg aggaggttca gtgatgagca     960
```

```
gattaaatca ttagaaacca tgttcgagaa cgagactaaa ttggaaccaa gaaagaaact   1020
gcagttagca cgagaactgg gattacaacc tcgtcaggtt gcaatttggt ttcagaacaa   1080
gagagctcga tggaaatcca agcaactcga gagggattac aacatactta agtccaattt   1140
tgataatctt gcttcccagt acaactcctt aaagaaagaa accaatcct tgcttttgca    1200 gttgcaaaag ctgaatgatc tgatgcagaa atccgagaaa aagagggggc agtactgttc   1260
aattggcttt gatcaggagt cgtataacag agaggataat actattaaga ataaggaaat   1320
ggaagggaag ccaagcttgt catttgattt atcagagcat ggagttaatg gtgtaatttc   1380
agatgatgac agtagtataa aggctgatta tttcggcttg gatgaagaat ctgatcatct   1440
actgaaaatg gtagaagcag gggatagttc tttaacttcc cctgaaaact ggggtaccct   1500
agaggatgat ggtctcttgg accagcagcc taatagttgt aattatgatc agtggtggga   1560
tttctggtct tgaaccataa ttattattgc accatagaca aaaatatatc catctagacc   1620
ttggctttga ggggaagttc ataacatata acagatgcca gcgtctgtaa catttgagca   1680
cctcaacgtc caccaatccg tcgtttcttt cacaccataa gtggatgagt ggcatagttg   1740
agtttacctc agcttagggt catagcactg ttcatataga gaaaaaaact gaatgctttt   1800
accataatag aggctttact atcagaagcc cttttctact ggac                    1844

<210> SEQ ID NO 6
<211> LENGTH: 759
<212> TYPE: DNA
<213> ORGANISM: Nicotiana benthamiana

<400> SEQUENCE: 6
atgtttgatg tagggggaatt ttcttgtact tcttcagcag ctgctcttaa ttctgcagag    60
tgtttcagta gtggcagctt cagcagttta ccatcctcaa agaagaagaa ggttaataac   120
aagaatacga ggaggttcag tgatgagcag attaaatcat tagaaaccat gttcgagaac   180
gagactaaat tggaaccaag aaagaaactg cagttagcac gagaactggg attacaacct   240
cgtcaggttg caatttggtt tcagaacaag agagctcgat ggaaatccaa gcaactcgag   300
agggattaca acatacttaa gtccaatttt gataatcttg cttcccagta caactcctta   360
aagaaagaaa ccaatccctt gcttttgcag ttgcaaaagc tgaatgatct gatgcagaaa   420
tccgagaaag aagagggggca gtactgttca attggctttg atcaggagtc gtataacaga   480
gaggataata ctattaagaa taaggaaatg aagggaagc caagcttgtc atttgattta   540
tcagagcatg gagttaatgg tgtaatttca gatgatgaca gtagtataaa ggctgattat   600
ttcggcttgg atgaagaatc tgatcatcta ctgaaaatgg tagaagcagg ggatagttct   660
ttaacttccc ctgaaaactg ggggtaccta gaggatgatg gtctcttgga ccagcagcct   720
aatagttgta attatgatca gtggtgggat ttctggtct                           759

<210> SEQ ID NO 7
<211> LENGTH: 253
<212> TYPE: PRT
<213> ORGANISM: Nicotiana benthamiana

<400> SEQUENCE: 7

Met Phe Asp Val Gly Glu Phe Ser Cys Thr Ser Ser Ala Ala Ala Leu
1               5                   10                  15

Asn Ser Ala Glu Cys Phe Ser Ser Gly Ser Phe Ser Ser Leu Pro Ser
            20                  25                  30
```

Ser Lys Lys Lys Val Asn Asn Lys Asn Thr Arg Arg Phe Ser Asp
    35                  40                  45

Glu Gln Ile Lys Ser Leu Glu Thr Met Phe Glu Asn Glu Thr Lys Leu
50                  55                  60

Glu Pro Arg Lys Lys Leu Gln Leu Ala Arg Glu Leu Gly Leu Gln Pro
65                  70                  75                  80

Arg Gln Val Ala Ile Trp Phe Gln Asn Lys Arg Ala Arg Trp Lys Ser
                85                  90                  95

Lys Gln Leu Glu Arg Asp Tyr Asn Ile Leu Lys Ser Asn Phe Asp Asn
            100                 105                 110

Leu Ala Ser Gln Tyr Asn Ser Leu Lys Lys Glu Asn Gln Ser Leu Leu
        115                 120                 125

Leu Gln Leu Gln Lys Leu Asn Asp Leu Met Gln Lys Ser Glu Lys Glu
    130                 135                 140

Glu Gly Gln Tyr Cys Ser Ile Gly Phe Asp Gln Glu Ser Tyr Asn Arg
145                 150                 155                 160

Glu Asp Asn Thr Ile Lys Asn Lys Glu Met Glu Gly Lys Pro Ser Leu
                165                 170                 175

Ser Phe Asp Leu Ser Glu His Gly Val Asn Gly Val Ile Ser Asp Asp
            180                 185                 190

Asp Ser Ser Ile Lys Ala Asp Tyr Phe Gly Leu Asp Glu Glu Ser Asp
        195                 200                 205

His Leu Leu Lys Met Val Glu Ala Gly Asp Ser Ser Leu Thr Ser Pro
    210                 215                 220

Glu Asn Trp Gly Thr Leu Glu Asp Asp Gly Leu Leu Asp Gln Gln Pro
225                 230                 235                 240

Asn Ser Cys Asn Tyr Asp Gln Trp Trp Asp Phe Trp Ser
                245                 250

<210> SEQ ID NO 8
<211> LENGTH: 2401
<212> TYPE: DNA
<213> ORGANISM: Nicotiana benthamiana

<400> SEQUENCE: 8
gcacgaggct ccttatcacc aaacaattct tggggttttt aatatatacc caaaaaaaac      60
ttcctctcca ttttccctct ctatatcaag aatcaaacag atctgaattg atttgtctgt     120
tttttcttg attttgttat atggaatgac ggattgtaga agaccaacga tgactaatat     180
atggagcaat actacatccg atgataatat gatggaagct ttttatcttc tgatccgtc     240
gtcgttttgg gctggaacta ctactacacc aactcctcgg agttcagttt ctccggcgcc     300
ggcgccggtg acggggattg ccgtagaccc attaacatct atgccatatt caaccaaga     360
gtcactgcaa cagcgacttc agactttaat cgacggggct cgcgaagcgt ggacgtatgc     420
catattctgg caatcgtctg ttgtggattt cacgacccac tcggttttgg ggtggggaga     480
tgggtattat aaaggtgaag aagataaaaa taagcgcaaa acgcgtcgt tttcgcctga     540
ttttatcacg gagcaagcac accggaaaaa ggttctccgg gagctgaatt gtttaatttc     600
cggcacacaa actggtggtg aaaatgatgc tgtagatgaa gaagtaacgg atactgaatg     660
gttttttctg atttccatga ctcaatcgtt cgttaacgga agcgggcttc cgggcctggc     720
gatgtacagc tcaagcccga tttgggttac tggagcagag agattagctg cttcgcactg     780
tgaacgggcc cgacaggccc aaggtttcgg gcttcagact attgtttgta ttccttcagg     840
taatggtgtt gttgagctcg ggtcaactga gttgatattc cagactgctg atttaatgaa     900

-continued

```
caaggttaaa gttttgttta attttaatat tgatatgggt gcgactacgg gctcaggatc    960
gggctcatgt gctattcagg ccgagcccga tacttcagcc ctttggctga cggatccagc    1020
ttcctcagct gtggaagtca aggattcgtc taatacagtt ccttcaagta atagcagtaa    1080
gcaacttgtg tttggaaatg agaattctga aaatggtaat caaaattctc agcaaacaca    1140
aggatttttc accagggagt tgaattttc cgaatatgga tttgatggaa gtaatactcg    1200
gaatgggaat gtgaattctt cgcgttcttg ccagcctgag tctggtgaaa tcttgaattt    1260
tggtgatagt actaagagaa gtgcttcaag tgcaaatggg agcttgtttt cgggccaatc    1320
acagtttggg cccgggcccg cggaggagaa caagaacaag aacaagaaaa ggtcacctgc    1380
atcaagagga agcaacgatg aaggaatgct ttcatttgtt tcgggtgtga ttttgccaag    1440
ttcaaacacg gggaagtctg gtggaggtgg cgattcggat caatcagatc tcgaggcttc    1500
ggtggtgaag gaagcggata gtagtagagt tgtagacccg gagaagaagc cgaggaaacg    1560
agggaggaaa ccggctaacg ggagagagga gccattgaat catgtggagg cagagaggca    1620
aaggagggag aaattaaatc aaagattcta tgcacttaga gcagttgtac caaatgtgtc    1680
aaaaatggat aaagcatcac ttcttggtga tgcaattgca tttatcaatg agttgaaatc    1740
aaaggttcag aattctgact cagataaaga ggagttgagg aaccaaattg aatctttaag    1800
gaatgaatta gccaacaagg gatcaaaacta taccggtcct ccaccgttaa atcaagaact    1860
caagattgta gatatggata tcgacgttaa ggtgatcgga tgggatgcta tgattcgtat    1920
acaatctaat aaaagaacc atccagccgc gaagttaatg ccgctctca tggaattgga    1980
cttagatgtg caccatgcta gtgtttcagt ggtcaacgag ttgatgatcc aacaagcaac    2040
tgtgaaaatg gggagtcggc tttacacgca agaacaactt cggatatcat tgacatctag    2100
aattgctgaa tcgcgatgaa gagaaataca gtaaatggaa attatcatag tgagctttga    2160
ataatgttat ctttcattga gctattttaa gagaatttct catattgtta gatcttgagt    2220
ttaaggctac ttaaagtgca aagctaattg agctttcctt ttagtttttg ggtattttc    2280
aacttctata tttagtttgt tttccacatt ttctgtacat aaaaatgtga aaccaatact    2340
agatttcaag ttcttgcatt tagttcatgt aattagaaat aaatatgcag cttcatcttt    2400
t                                                                     2401
```

<210> SEQ ID NO 9
<211> LENGTH: 1971
<212> TYPE: DNA
<213> ORGANISM: Nicotiana benthamiana

<400> SEQUENCE: 9

```
atgacggatt gtagaagacc aacgatgact aatatatgga gcaatactac atccgatgat     60
aatatgatgg aagctttttt atcttctgat ccgtcgtcgt tttgggctgg aactactact    120
acaccaactc ctcggagttc agtttctccg gcgccggcgc cggtgacggg gattgccgta    180
gacccattaa catctatgcc atatttcaac caagagtcac tgcaacagcg acttcagact    240
ttaatcgacg gggctcgcga agcgtggacg tatgccatat tctggcaatc gtctgttgtg    300
gatttcacga cccactcggt tttggggtgg ggagatgggt attataaagg tgaagaagat    360
aaaaataagc gcaaaacggc gtcgttttcg cctgattta tcacggagca agcacaccgg    420
aaaaaggttc tccgggagct gaattgttta atttccggca cacaaactgg tggtgaaaat    480
gatgctgtag atgaagaagt aacgggatact gaatggtttt ttctgatttc catgactcaa    540
tcgttcgtta acggaagcgg gcttccgggc ctggcgatgt acagctcaag cccgatttgg    600
```

| | |
|---|---|
| gttactggag cagagagatt agctgcttcg cactgtgaac gggcccgaca ggcccaaggt | 660 |
| ttcgggcttc agactattgt ttgtattcct tcaggtaatg gtgttgttga gctcgggtca | 720 |
| actgagttga tattccagac tgctgattta atgaacaagg ttaaagtttt gtttaatttt | 780 |
| aatattgata tgggtgcgac tacgggctca ggatcgggct catgtgctat tcaggccgag | 840 |
| cccgatactt cagccctttg gctgacggat ccagcttcct cagctgtgga agtcaaggat | 900 |
| tcgtctaata cagttccttc aagtaatagc agtaagcaac ttgtgtttgg aaatgagaat | 960 |
| tctgaaaatg gtaatcaaaa ttctcagcaa acacaaggat ttttcaccag ggagttgaat | 1020 |
| ttttccgaat atggatttga tggaagtaat actcggaatg gaatgtgaa ttcttcgcgt | 1080 |
| tcttgccagc ctgagtctgg tgaaatcttg aattttggtg atagtactaa gagaagtgct | 1140 |
| tcaagtgcaa atgggagctt gttttcgggc caatcacagt ttgggcccgg gcccgcggag | 1200 |
| gagaacaaga acaagaacaa gaaaaggtca cctgcatcaa gaggaagcaa cgatgaagga | 1260 |
| atgctttcat ttgtttcggg tgtgattttg ccaagttcaa acacggggaa gtctggtgga | 1320 |
| ggtggcgatt cggatcaatc agatctcgag gcttcggtgg tgaaggaagc ggatagtagt | 1380 |
| agagttgtag acccggagaa gaagccgagg aaacgaggga ggaaaccggc taacgggaga | 1440 |
| gaggagccat tgaatcatgt ggaggcagag aggcaaagga gggagaaatt aaatcaaaga | 1500 |
| ttctatgcac ttagagcagt tgtaccaaat gtgtcaaaaa tggataaagc atcacttctt | 1560 |
| ggtgatgcaa ttgcatttat caatgagttg aaatcaaagg ttcagaattc tgactcagat | 1620 |
| aaagaggagt tgaggaacca aattgaatct ttaaggaatg aattagccaa caagggatca | 1680 |
| aactataccg gtcctccacc gttaaatcaa gaactcaaga ttgtagatat ggatatcgac | 1740 |
| gttaaggtga tcggatggga tgctatgatt cgtatacaat ctaataaaaa gaaccatcca | 1800 |
| gccgcgaagt taatggccgc tctcatggaa ttggacttag atgtgcacca tgctagtgtt | 1860 |
| tcagtggtca acgagttgat gatccaacaa gcaactgtga aaatggggag tcggctttac | 1920 |
| acgcaagaac aacttcggat atcattgaca tctagaattg ctgaatcgcg a | 1971 |

<210> SEQ ID NO 10
<211> LENGTH: 657
<212> TYPE: PRT
<213> ORGANISM: Nicotiana benthamiana

<400> SEQUENCE: 10

```
Met Thr Asp Cys Arg Arg Pro Thr Met Thr Asn Ile Trp Ser Asn Thr
1               5                   10                  15

Thr Ser Asp Asp Asn Met Met Glu Ala Phe Leu Ser Ser Asp Pro Ser
                20                  25                  30

Ser Phe Trp Ala Gly Thr Thr Thr Pro Thr Pro Arg Ser Ser Val
            35                  40                  45

Ser Pro Ala Pro Ala Pro Val Thr Gly Ile Ala Val Asp Pro Leu Thr
        50                  55                  60

Ser Met Pro Tyr Phe Asn Gln Glu Ser Leu Gln Gln Arg Leu Gln Thr
65                  70                  75                  80

Leu Ile Asp Gly Ala Arg Glu Ala Trp Thr Tyr Ala Ile Phe Trp Gln
                85                  90                  95

Ser Ser Val Val Asp Phe Thr Thr His Ser Val Leu Gly Trp Gly Asp
            100                 105                 110

Gly Tyr Tyr Lys Gly Glu Glu Asp Lys Asn Lys Arg Lys Thr Ala Ser
        115                 120                 125
```

```
Phe Ser Pro Asp Phe Ile Thr Glu Gln Ala His Arg Lys Lys Val Leu
130                 135                 140
Arg Glu Leu Asn Cys Leu Ile Ser Gly Thr Gln Thr Gly Gly Glu Asn
145                 150                 155                 160
Asp Ala Val Asp Glu Val Thr Asp Thr Glu Trp Phe Phe Leu Ile
                165                 170                 175
Ser Met Thr Gln Ser Phe Val Asn Gly Ser Gly Leu Pro Gly Leu Ala
            180                 185                 190
Met Tyr Ser Ser Ser Pro Ile Trp Val Thr Gly Ala Glu Arg Leu Ala
            195                 200                 205
Ala Ser His Cys Glu Arg Ala Arg Gln Ala Gln Gly Phe Gly Leu Gln
210                 215                 220
Thr Ile Val Cys Ile Pro Ser Gly Asn Gly Val Val Glu Leu Gly Ser
225                 230                 235                 240
Thr Glu Leu Ile Phe Gln Thr Ala Asp Leu Met Asn Lys Val Lys Val
                245                 250                 255
Leu Phe Asn Phe Asn Ile Asp Met Gly Ala Thr Thr Gly Ser Gly Ser
            260                 265                 270
Gly Ser Cys Ala Ile Gln Ala Glu Pro Asp Thr Ser Ala Leu Trp Leu
    275                 280                 285
Thr Asp Pro Ala Ser Ser Ala Val Glu Val Lys Asp Ser Ser Asn Thr
290                 295                 300
Val Pro Ser Ser Asn Ser Ser Lys Gln Leu Val Phe Gly Asn Glu Asn
305                 310                 315                 320
Ser Glu Asn Gly Asn Gln Asn Ser Gln Gln Thr Gln Gly Phe Phe Thr
            325                 330                 335
Arg Glu Leu Asn Phe Ser Glu Tyr Gly Phe Asp Gly Ser Asn Thr Arg
            340                 345                 350
Asn Gly Asn Val Asn Ser Ser Arg Ser Cys Gln Pro Glu Ser Gly Glu
            355                 360                 365
Ile Leu Asn Phe Gly Asp Ser Thr Lys Arg Ser Ala Ser Ser Ala Asn
370                 375                 380
Gly Ser Leu Phe Ser Gly Gln Ser Gln Phe Gly Pro Gly Pro Ala Glu
385                 390                 395                 400
Glu Asn Lys Asn Lys Asn Lys Lys Arg Ser Pro Ala Ser Arg Gly Ser
            405                 410                 415
Asn Asp Glu Gly Met Leu Ser Phe Val Ser Gly Val Ile Leu Pro Ser
            420                 425                 430
Ser Asn Thr Gly Lys Ser Gly Gly Gly Asp Ser Asp Gln Ser Asp
            435                 440                 445
Leu Glu Ala Ser Val Val Lys Glu Ala Asp Ser Ser Arg Val Val Asp
450                 455                 460
Pro Glu Lys Lys Pro Arg Lys Arg Gly Arg Lys Pro Ala Asn Gly Arg
465                 470                 475                 480
Glu Glu Pro Leu Asn His Val Glu Ala Glu Arg Gln Arg Arg Glu Lys
            485                 490                 495
Leu Asn Gln Arg Phe Tyr Ala Leu Arg Ala Val Val Pro Asn Val Ser
            500                 505                 510
Lys Met Asp Lys Ala Ser Leu Leu Gly Asp Ala Ile Ala Phe Ile Asn
            515                 520                 525
Glu Leu Lys Ser Lys Val Gln Asn Ser Asp Ser Asp Lys Glu Glu Leu
530                 535                 540
```

```
Arg Asn Gln Ile Glu Ser Leu Arg Asn Glu Leu Ala Asn Lys Gly Ser
545                 550                 555                 560

Asn Tyr Thr Gly Pro Pro Leu Asn Gln Glu Leu Lys Ile Val Asp
            565                 570                 575

Met Asp Ile Asp Val Lys Val Ile Gly Trp Asp Ala Met Ile Arg Ile
            580                 585                 590

Gln Ser Asn Lys Lys Asn His Pro Ala Ala Lys Leu Met Ala Ala Leu
        595                 600                 605

Met Glu Leu Asp Leu Asp Val His His Ala Ser Val Ser Val Val Asn
610                 615                 620

Glu Leu Met Ile Gln Gln Ala Thr Val Lys Met Gly Ser Arg Leu Tyr
625                 630                 635                 640

Thr Gln Glu Gln Leu Arg Ile Ser Leu Thr Ser Arg Ile Ala Glu Ser
            645                 650                 655

Arg
```

<210> SEQ ID NO 11
<211> LENGTH: 958
<212> TYPE: DNA
<213> ORGANISM: Nicotiana benthamiana

<400> SEQUENCE: 11

```
ctggagcacg aggacactga catggactga aggagtagaa agactggagc acgaggacac     60
tgacatggac tgaaggagta gaaaatccag aattaataaa ccctagttat cagcaaaggt    120
gcaagaaaca tttgttccaa aactctaaga gaaaagaaaa tgaattcagc agatgtaacc    180
ttctcttttct ctgattttaa tctccttgaa tccataaagc aacatcttct gaatgattca    240
gattttctg aaattatttc gccgatgagt tcaagtaacg cattgcctaa cagtcctagt    300
tcaggttttg gcagctcccc ttcagcagaa aatagcttcg aaatctccct ttgggctgaa    360
aactttgagg aaacaatacc aaatctcgaa gaaaagtgcg agtccgaaga ggaaacgaag    420
gggaacgtgg tggcgcgtga aacaacgcg ccgcaagatt ggaggcggta cataggagtg    480
aaacggcgac catgggggac attttcagcg gagatcagag accccaatag gagaggggcc    540
agactgtggt taggaactta cgagaccgca gaggacgcag cgttggctta cgatcaagcc    600
gctttcaaaa tccgcggctc gagagctcgg ctcaattttc ctcacttaat cggctcaaac    660
atgcgtaagc cggctagagt tacagagaga cgtagtcgta cgcgctcacc cgagccatcg    720
tcttcttcgt ccacctcatc atcagtaaat gtaccgagaa aaggaaaat agatgtgata    780
aattccatag ccacggtttg tcatggttgg aacctccaga tgttactgta actatatttg    840
gaaggatatt tagtgtttta gtattagaat aacaatgttt attttagaaa gcttactccc    900
tcttagcccg ctaacttcaa gctgggcact taaagcattg gttaattgtt aattttttc    958
```

<210> SEQ ID NO 12
<211> LENGTH: 669
<212> TYPE: DNA
<213> ORGANISM: Nicotiana benthamiana

<400> SEQUENCE: 12

```
atgaattcag cagatgtaac cttctctttc tctgatttta atctccttga atccataaag     60
caacatcttc tgaatgattc agattttct gaaattattt cgccgatgag ttcaagtaac    120
gcattgccta acagtcctag ttcaggtttt ggcagctccc cttcagcaga aaatagcttc    180
gaaatctccc tttgggctga aaactttgag gaaacaatac caaatctcga agaaaagtgc    240
```

```
gagtccgaag aggaaacgaa ggggaacgtg gtggcgcgtg agaacaacgc gccgcaagat    300
tggaggcggt acataggagt gaaacggcga ccatggggga catttcagc ggagatcaga    360
gaccccaata ggagaggggc cagactgtgg ttaggaactt acgagaccgc agaggacgca    420
gcgttggctt acgatcaagc cgcttttcaaa atccgcggct cgagagctcg gctcaatttt    480
cctcacttaa tcggctcaaa catgcgtaag ccggctagag ttacagagag acgtagtcgt    540
acgcgctcac ccgagccatc gtcttcttcg tccacctcat catcagtaaa tgtaccgaga    600
aaaaggaaaa tagatgtgat aaattccata gccacggttt gtcatggttg gaacctccag    660
atgttactg                                                           669
```

```
<210> SEQ ID NO 13
<211> LENGTH: 223
<212> TYPE: PRT
<213> ORGANISM: Nicotiana benthamiana

<400> SEQUENCE: 13
```

```
Met Asn Ser Ala Asp Val Thr Phe Ser Phe Ser Asp Phe Asn Leu Leu
1               5                   10                  15
Glu Ser Ile Lys Gln His Leu Leu Asn Asp Ser Asp Phe Ser Glu Ile
            20                  25                  30
Ile Ser Pro Met Ser Ser Ser Asn Ala Leu Pro Asn Ser Pro Ser Ser
        35                  40                  45
Gly Phe Gly Ser Ser Pro Ser Ala Glu Asn Ser Phe Glu Ile Ser Leu
    50                  55                  60
Trp Ala Glu Asn Phe Glu Glu Thr Ile Pro Asn Leu Glu Glu Lys Cys
65                  70                  75                  80
Glu Ser Glu Glu Glu Thr Lys Gly Asn Val Val Ala Arg Glu Asn Asn
                85                  90                  95
Ala Pro Gln Asp Trp Arg Arg Tyr Ile Gly Val Lys Arg Arg Pro Trp
            100                 105                 110
Gly Thr Phe Ser Ala Glu Ile Arg Asp Pro Asn Arg Arg Gly Ala Arg
        115                 120                 125
Leu Trp Leu Gly Thr Tyr Glu Thr Ala Glu Asp Ala Ala Leu Ala Tyr
    130                 135                 140
Asp Gln Ala Ala Phe Lys Ile Arg Gly Ser Arg Ala Arg Leu Asn Phe
145                 150                 155                 160
Pro His Leu Ile Gly Ser Asn Met Arg Lys Pro Ala Arg Val Thr Glu
                165                 170                 175
Arg Arg Ser Arg Thr Arg Ser Pro Glu Pro Ser Ser Ser Ser Ser Thr
            180                 185                 190
Ser Ser Ser Val Asn Val Pro Arg Lys Arg Lys Ile Asp Val Ile Asn
        195                 200                 205
Ser Ile Ala Thr Val Cys His Gly Trp Asn Leu Gln Met Leu Leu
    210                 215                 220
```

```
<210> SEQ ID NO 14
<211> LENGTH: 3298
<212> TYPE: DNA
<213> ORGANISM: Nicotiana benthamiana

<400> SEQUENCE: 14
```

```
ctttcctttc ttctgtagct ttcaatatgt gaaaagaaa atcactgaaa agaaaaaga     60
aaagaaaaag ggaaaaaagt acagctgata gagagagaga gaaagagatc tactgaaata    120
gccaacttga gctcttgcag aaatcttgaa gtagccaaaa agttgcttct tttactgtgc    180
```

-continued

```
tctctactta gttttaactc ataccccac  tttctttaag ggtttcaaga tctgcttcag   240 tttttgcta  agctcagttg ctgacttgct tctgtagctt atttcaagaa aagggtattt   300
agggtttgtg  tagttttttg tgtgtttgtt ttattttcca gtgagtaatt gaagatctgg   360
ggacaagtat  gaagcagttt ttaatggtgg tatttagttg tggaagtggg tttggatgaa   420
aaatatggtt  tcttgctgct tggttttgc  ttggggtggg gggtgggggc tgtactaaaa   480
agactaaagt  tttcatttt  tttggttttt tatattttt  gagagctgcc cttttgggt    540 tatttgttta  actagtgaaa gtaggttctt gataggagtt agtttgattt gctgtaatga   600
gggtatcttc  agctgggttt aatcctcaac cagaggaagc agcaggggag aagaaatgcc   660
tgaattcaga  gctgtggcac gcctgtgccg ggccactagt ttcgcttcct cctgtaggaa   720
gcggagttgt  gtattttccc caagggcata gtgaacaggt tgctgcctcg acaaacaagg   780
aagtggatgc  tcatatccct aactatcctg gtttaccacc tcagctaatt tgtcagcttc   840
acaacctgac  aatgcatgca gatgttgaga ccgatgaagt atatgctcaa atgacgttgc   900
agccactaag  tgcacaagag caaaggatg  tgtgcctgct accagcagaa cttggcatcc   960
cgagtaaaca  accaaccaat tatttctgca aaaccttgac ggcaagtgac accagtactc  1020
atggtggatt  ctctgtcccc cgacgtgcag cagaaaagt  ttttccccct cttgattact  1080
ctcagcagcc  gccctgtcaa gagttgattg caaaagatct ccatggaaat gaatggaaat  1140
tccggcatat  ttttcgtggc caaccaaaga ggcatctatt gacaacagga tggagtgtgt  1200
tcgtaagtgc  aaagagactt gttgcgggcg atgcagtcat ctttatctgg aatgaaaata  1260
atcaattgct  ttggggatt  cgacgtgcta atcgtcctca aacagttatg ccttcttcag  1320
ttttgtcaag  tgatagcatg cacattggtc tccttgctgc ggcggctcat gcagctgcaa  1380
ctaatagccg  ctttacaata ttttataatc caagggcaag tccatcagag tttgtcatac  1440
ctcttgccaa  gtatgctaaa gcagtttatc atacacggat ttctgttggt atgaggttcc  1500
ggatgctgtt  tgaaacagaa gaatcgagcg tccgtaggta tatgggcaca attactggta  1560
tcagtgattt  agatcctgtt cgttggccaa attcacattg gcggtctgtg aaggttggat  1620
gggatgaatc  aactgcagga gagaggcagc ccagagtttc gctgtgggaa attgaacctc  1680
tgacaacttt  tcctatgtat ccttctcctt tctcccttag gctaaaaagg ccttggcctt  1740
ctctccctgg  ttttcccaat ggtgatatga ctatgaattc tccactctcg tggctgcgtg  1800
gtgacatagg  agatcaaggg attcagtcgc ttaatttcca gggatatggt gttactccgt  1860
ttatgcagcc  aagaattgat gcttctatgt taggtttgca acctgacatt ctgcaaacaa  1920
tggctgcact  agatccttcg aaatttgcaa atcaatcctt tatgcagttc caacaaagta  1980
tacctggcgt  ttcagcatct ttgagtcata gtcagatttt gcagccttct cattcacagc  2040
aaaatctgct  ccacggcttc tccgaaaacc agttaatatc tcaggcacag atgcttcagc  2100
aacaattgca  gcgccgtcag aattataatg atcagcagca attgctgcag ccacagcttc  2160
agcaacacca  ggaagtgaac tcctcgcagt ttcaacatca acagcaaacc aaggccatgt  2220
ccagtctctc  tcagatgaca tcggctgcgc agccccagct ttctcatttg caagtcttaa  2280
gttcaactgg  ttctccacaa acattttctg atatacttgg taaccatgtc aatgcatcta  2340
gtaattctac  tatgcagagt ctgttgagtt cattttcccg tgatggagcg tctgctgtcc  2400
ttaacatgca  tgaagctcac cctctagtgt cttcttcctc atcatcaaaa cgaattgctc  2460
tagaatctca  gctcccttct cgggttactc cattcgctgt gccccagcct gaggatgtga  2520
tatcacacaa  tactaaagtc tctgatctct cctctctgtt gcctcctctt cctggcagag  2580
```

-continued

| | |
|---|---|
| aatctttttc tgattataga ggagtagaag atagccaaaa caatgcgatg tatggattta | 2640 |
| atacagactg tttgaacata ctgcagaacg gtatgtccaa catgaaggat agtactggtg | 2700 |
| ataatggatc tttatctatt ccttatgcta cctctacctt cacaaatact gtgggcaacg | 2760 |
| agtatcccat taactcagac atgacaactt caagttgtgt agatgaatca ggtttcttgc | 2820 |
| agtcctctga aaatggagac caacgaaacc caaccaatag aacctttgtg aaggttcata | 2880 |
| aatcagggtc ctttggacga tcactcgata tctccaagtt tagcaactat catgaacttc | 2940 |
| gaagtgagct tgctcacatg tttgggctag aaggcttgtt ggaggaccct gaaagatcag | 3000 |
| gctggcagct tgtatttgta gaccgagaga atgatgttct cctcctcggt gacgatccct | 3060 |
| ggcaggagtt tgtgaacaat gtttggtaca tcaagatact ttctccgctc gaagtgcaac | 3120 |
| agatggggaa agacggcctt gatcttccaa atgctggcct agcacaaagg cttcctagca | 3180 |
| atggcgtcgg atgtgatgac tatatgaacc aaaagggctc ccgaaatacc atgaacggga | 3240 |
| taccctgggg gtcgcttgat tactaatgat tagtagtgac cccttgccaa aggtaatt | 3298 |

<210> SEQ ID NO 15
<211> LENGTH: 2667
<212> TYPE: DNA
<213> ORGANISM: Nicotiana benthamiana

<400> SEQUENCE: 15

| | |
|---|---|
| atgagggtat cttcagctgg gtttaatcct caaccagagg aagcagcagg ggagaagaaa | 60 |
| tgcctgaatt cagagctgtg gcacgcctgt gccgggccac tagtttcgct tcctcctgta | 120 |
| ggaagcggag ttgtgtattt tccccaaggg catagtgaac aggttgctgc ctcgacaaac | 180 |
| aaggaagtgg atgctcatat ccctaactat cctggtttac cacctcagct aatttgtcag | 240 |
| cttcacaacc tgacaatgca tgcagatgtt gagaccgatg aagtatatgc tcaaatgacg | 300 |
| ttgcagccac taagtgcaca agagcaaaag gatgtgtgcc tgctaccagc agaacttggc | 360 |
| atcccgagta acaaccaac caattatttc tgcaaaacct tgacggcaag tgacaccagt | 420 |
| actcatggtg gattctctgt ccccccgacgt gcagcagaaa aagttttttcc ccctcttgat | 480 |
| tactctcagc agccgccctg tcaagagttg attgcaaaag atctccatgg aaatgaatgg | 540 |
| aaattccggc atatttttcg tggccaacca agaggcatc tattgacaac aggatggagt | 600 |
| gtgttcgtaa gtgcaaagag acttgttgcg ggcgatgcag tcatctttat ctggaatgaa | 660 |
| ataatcaat tgcttttggg gattcgacgt gctaatcgtc ctcaaacagt tatgccttct | 720 |
| tcagttttgt caagtgatag catgcacatt ggtctccttg ctgcggcggc tcatgcagct | 780 |
| gcaactaata gccgctttac aatatttttat aatccaaggg caagtccatc agagtttgtc | 840 |
| atacctcttg ccaagtatgc taaagcagtt tatcatacac ggatttctgt tggtatgagg | 900 |
| ttccggatgc tgtttgaaac agaagaatcg agcgtccgta ggtatatggg cacaattact | 960 |
| ggtatcagtg atttagatcc tgttcgttgg ccaaattcac attggcggtc tgtgaaggtt | 1020 |
| ggatgggatg aatcaactgc aggagagagg cagcccagag tttcgctgtg ggaaattgaa | 1080 |
| cctctgacaa ctttttcctat gtatccttct ccttttctccc ttaggctaaa aaggccttgg | 1140 |
| ccttctctcc ctggttttcc caatggtgat atgactatga attctccact ctcgtggctg | 1200 |
| cgtggtgaca taggagatca agggattcag tcgcttaatt tccagggata tggtgttact | 1260 |
| ccgtttatgc agccaagaat tgatgcttct atgttaggtt tgcaacctga cattctgcaa | 1320 |
| acaatggctg cactagatcc ttcgaaattt gcaaatcaat cctttatgca gttccaacaa | 1380 |
| agtataccctg gcgtttcagc atctttgagt catagtcaga ttttgcagcc ttctcattca | 1440 |

```
cagcaaaatc tgctccacgg cttctccgaa aaccagttaa tatctcaggc acagatgctt   1500
cagcaacaat tgcagcgccg tcagaattat aatgatcagc agcaattgct gcagccacag   1560
cttcagcaac accaggaagt gaactcctcg cagtttcaac atcaacagca aaccaaggcc   1620
atgtccagtc tctctcagat gacatcggct gcgcagcccc agctttctca tttgcaagtc   1680
ttaagttcaa ctggttctcc acaaacattt tctgatatac ttggtaacca tgtcaatgca   1740
tctagtaatt ctactatgca gagtctgttg agttcatttt cccgtgatgg agcgtctgct   1800
gtccttaaca tgcatgaagc tcaccctcta gtgtcttctt cctcatcatc aaaacgaatt   1860
gctctagaat ctcagctccc ttctcgggtt actccattcg ctgtgcccca gcctgaggat   1920
gtgatatcac acaatactaa agtctctgat ctctcctctc tgttgcctcc tcttcctggc   1980
agagaatctt tttctgatta tagaggagta gaagatagcc aaaacaatgc gatgtatgga   2040
tttaatacag actgtttgaa catactgcag aacggtatgt ccaacatgaa ggatagtact   2100
ggtgataatg gatctttatc tattccttat gctacctcta ccttcacaaa tactgtgggc   2160
aacgagtatc ccattaactc agacatgaca acttcaagtt gtgtagatga atcaggtttc   2220
ttgcagtcct ctgaaaatgg agaccaacga aacccaacca atagaacctt tgtgaaggtt   2280
cataaatcag ggtcctttgg acgatcactc gatatctcca agtttagcaa ctatcatgaa   2340
cttcgaagtg agcttgctca catgtttggg ctagaaggct tgttggagga ccctgaaaga   2400
tcaggctggc agcttgtatt tgtagaccga gagaatgatg ttctcctcct cggtgacgat   2460
ccctggcagg agtttgtgaa caatgtttgg tacatcaaga actttctcc gctcgaagtg   2520 caacagatgg ggaaagacgg ccttgatctt ccaaatgctg gcctagcaca aaggcttcct   2580
agcaatggcg tcggatgtga tgactatatg aaccaaaagg gctcccgaaa taccatgaac   2640
gggataccct tggggtcgct tgattac                                      2667
```

<210> SEQ ID NO 16
<211> LENGTH: 889
<212> TYPE: PRT
<213> ORGANISM: Nicotiana benthamiana

<400> SEQUENCE: 16

```
Met Arg Val Ser Ser Ala Gly Phe Asn Pro Gln Pro Glu Glu Ala Ala
1               5                   10                  15

Gly Glu Lys Lys Cys Leu Asn Ser Glu Leu Trp His Ala Cys Ala Gly
            20                  25                  30

Pro Leu Val Ser Leu Pro Pro Val Gly Ser Gly Val Val Tyr Phe Pro
        35                  40                  45

Gln Gly His Ser Glu Gln Val Ala Ala Ser Thr Asn Lys Glu Val Asp
    50                  55                  60

Ala His Ile Pro Asn Tyr Pro Gly Leu Pro Gln Leu Ile Cys Gln
65                  70                  75                  80

Leu His Asn Leu Thr Met His Ala Asp Val Glu Thr Asp Glu Val Tyr
                85                  90                  95

Ala Gln Met Thr Leu Gln Pro Leu Ser Ala Gln Glu Gln Lys Asp Val
            100                 105                 110

Cys Leu Leu Pro Ala Glu Leu Gly Ile Pro Ser Lys Gln Pro Thr Asn
        115                 120                 125

Tyr Phe Cys Lys Thr Leu Thr Ala Ser Asp Thr Ser His Gly Gly
    130                 135                 140

Phe Ser Val Pro Arg Arg Ala Ala Glu Lys Val Phe Pro Pro Leu Asp
145                 150                 155                 160
```

-continued

```
Tyr Ser Gln Gln Pro Pro Cys Gln Glu Leu Ile Ala Lys Asp Leu His
                165                 170                 175
Gly Asn Glu Trp Lys Phe Arg His Ile Phe Arg Gly Gln Pro Lys Arg
            180                 185                 190
His Leu Leu Thr Thr Gly Trp Ser Val Phe Val Ser Ala Lys Arg Leu
        195                 200                 205
Val Ala Gly Asp Ala Val Ile Phe Ile Trp Asn Glu Asn Asn Gln Leu
    210                 215                 220
Leu Leu Gly Ile Arg Arg Ala Asn Arg Pro Gln Thr Val Met Pro Ser
225                 230                 235                 240
Ser Val Leu Ser Ser Asp Ser Met His Ile Gly Leu Leu Ala Ala Ala
                245                 250                 255
Ala His Ala Ala Ala Thr Asn Ser Arg Phe Thr Ile Phe Tyr Asn Pro
            260                 265                 270
Arg Ala Ser Pro Ser Glu Phe Val Ile Pro Leu Ala Lys Tyr Ala Lys
        275                 280                 285
Ala Val Tyr His Thr Arg Ile Ser Val Gly Met Arg Phe Arg Met Leu
    290                 295                 300
Phe Glu Thr Glu Glu Ser Ser Val Arg Arg Tyr Met Gly Thr Ile Thr
305                 310                 315                 320
Gly Ile Ser Asp Leu Asp Pro Val Arg Trp Pro Asn Ser His Trp Arg
                325                 330                 335
Ser Val Lys Val Gly Trp Asp Glu Ser Thr Ala Gly Glu Arg Gln Pro
            340                 345                 350
Arg Val Ser Leu Trp Glu Ile Glu Pro Leu Thr Thr Phe Pro Met Tyr
        355                 360                 365
Pro Ser Pro Phe Ser Leu Arg Leu Lys Arg Pro Trp Pro Ser Leu Pro
    370                 375                 380
Gly Phe Pro Asn Gly Asp Met Thr Met Asn Ser Pro Leu Ser Trp Leu
385                 390                 395                 400
Arg Gly Asp Ile Gly Asp Gln Gly Ile Gln Ser Leu Asn Phe Gln Gly
                405                 410                 415
Tyr Gly Val Thr Pro Phe Met Gln Pro Arg Ile Asp Ala Ser Met Leu
            420                 425                 430
Gly Leu Gln Pro Asp Ile Leu Gln Thr Met Ala Ala Leu Asp Pro Ser
        435                 440                 445
Lys Phe Ala Asn Gln Ser Phe Met Gln Phe Gln Gln Ser Ile Pro Gly
    450                 455                 460
Val Ser Ala Ser Leu Ser His Ser Gln Ile Leu Gln Pro Ser His Ser
465                 470                 475                 480
Gln Gln Asn Leu Leu His Gly Phe Ser Glu Asn Gln Leu Ile Ser Gln
                485                 490                 495
Ala Gln Met Leu Gln Gln Leu Gln Arg Arg Gln Asn Tyr Asn Asp
            500                 505                 510
Gln Gln Gln Leu Leu Gln Pro Gln Leu Gln Gln His Gln Glu Val Asn
        515                 520                 525
Ser Ser Gln Phe Gln His Gln Gln Thr Lys Ala Met Ser Ser Leu
530                 535                 540
Ser Gln Met Thr Ser Ala Ala Gln Pro Gln Leu Ser His Leu Gln Val
545                 550                 555                 560
Leu Ser Ser Thr Gly Ser Pro Gln Thr Phe Ser Asp Ile Leu Gly Asn
                565                 570                 575
```

```
His Val Asn Ala Ser Ser Asn Ser Thr Met Gln Ser Leu Leu Ser Ser
                580                 585                 590

Phe Ser Arg Asp Gly Ala Ser Ala Val Leu Asn Met His Glu Ala His
            595                 600                 605

Pro Leu Val Ser Ser Ser Ser Ser Lys Arg Ile Ala Leu Glu Ser
        610                 615                 620

Gln Leu Pro Ser Arg Val Thr Pro Phe Ala Val Pro Gln Pro Glu Asp
625                 630                 635                 640

Val Ile Ser His Asn Thr Lys Val Ser Asp Leu Ser Ser Leu Leu Pro
                645                 650                 655

Pro Leu Pro Gly Arg Glu Ser Phe Ser Asp Tyr Arg Gly Val Glu Asp
            660                 665                 670

Ser Gln Asn Asn Ala Met Tyr Gly Phe Asn Thr Asp Cys Leu Asn Ile
        675                 680                 685

Leu Gln Asn Gly Met Ser Asn Met Lys Asp Ser Thr Gly Asp Asn Gly
690                 695                 700

Ser Leu Ser Ile Pro Tyr Ala Thr Ser Thr Phe Thr Asn Thr Val Gly
705                 710                 715                 720

Asn Glu Tyr Pro Ile Asn Ser Asp Met Thr Thr Ser Ser Cys Val Asp
                725                 730                 735

Glu Ser Gly Phe Leu Gln Ser Ser Glu Asn Gly Asp Gln Arg Asn Pro
            740                 745                 750

Thr Asn Arg Thr Phe Val Lys Val His Lys Ser Gly Ser Phe Gly Arg
        755                 760                 765

Ser Leu Asp Ile Ser Lys Phe Ser Asn Tyr His Glu Leu Arg Ser Glu
770                 775                 780

Leu Ala His Met Phe Gly Leu Glu Gly Leu Leu Glu Asp Pro Glu Arg
785                 790                 795                 800

Ser Gly Trp Gln Leu Val Phe Val Asp Arg Glu Asn Asp Val Leu Leu
                805                 810                 815

Leu Gly Asp Asp Pro Trp Gln Glu Phe Val Asn Asn Val Trp Tyr Ile
            820                 825                 830

Lys Ile Leu Ser Pro Leu Glu Val Gln Gln Met Gly Lys Asp Gly Leu
        835                 840                 845

Asp Leu Pro Asn Ala Gly Leu Ala Gln Arg Leu Pro Ser Asn Gly Val
850                 855                 860

Gly Cys Asp Asp Tyr Met Asn Gln Lys Gly Ser Arg Asn Thr Met Asn
865                 870                 875                 880

Gly Ile Pro Leu Gly Ser Leu Asp Tyr
                885

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tttttttttt tttttttttt ttttt                                                25

<210> SEQ ID NO 18
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 18
cgggatcctc gagcggccgc ccgggcaggt                                          30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cggaattcag cgtggtcgcg gccgaggt                                            28

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttactcaag gaagcacgat gag                                                 23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagtcgagaa tgtcaatctc gtag                                                24
```